(12) United States Patent
Tamura et al.

(10) Patent No.: US 9,365,501 B2
(45) Date of Patent: Jun. 14, 2016

(54) STABLE POLYMERIZABLE UV-ABSORBING COLORANT FOR INTRAOCULAR LENS

(71) Applicant: KOWA COMPANY, LTD., Aichi (JP)

(72) Inventors: Masahiro Tamura, Shizuoka (JP); Takahide Oshita, Shizuoka (JP)

(73) Assignee: KOWA COMPANY, LTD., Nagoya-shi, Aichi (JP)

( * ) Notice: Subject to any disclaimer, the term of this patent is extended or adjusted under 35 U.S.C. 154(b) by 0 days.

(21) Appl. No.: 14/397,352

(22) PCT Filed: Apr. 30, 2013

(86) PCT No.: PCT/JP2013/062537
§ 371 (c)(1),
(2) Date: Oct. 27, 2014

(87) PCT Pub. No.: WO2013/162042
PCT Pub. Date: Oct. 31, 2013

(65) Prior Publication Data
US 2015/0094439 A1     Apr. 2, 2015

(30) Foreign Application Priority Data

Apr. 27, 2012   (JP) ................................ 2012-102960

(51) Int. Cl.

| C07C 245/08 | (2006.01) |
|---|---|
| A61L 27/16 | (2006.01) |
| C08F 220/68 | (2006.01) |
| C09B 29/12 | (2006.01) |
| C08F 220/60 | (2006.01) |
| A61L 27/50 | (2006.01) |
| C09B 29/01 | (2006.01) |
| C09B 69/10 | (2006.01) |

(52) U.S. Cl.
CPC ............... *C07C 245/08* (2013.01); *A61L 27/16* (2013.01); *A61L 27/50* (2013.01); *C08F 220/60* (2013.01); *C08F 220/68* (2013.01); *C09B 29/0003* (2013.01); *C09B 29/12* (2013.01); *C09B 69/106* (2013.01); *A61L 2430/16* (2013.01)

(58) Field of Classification Search
CPC ..... A61L 27/16; A61L 27/50; A61L 2430/16; C07C 245/08; C08F 220/60; C08F 220/68; C09B 29/0003; C09B 29/12; C09B 69/106
USPC .................... 526/310, 304; 534/851
See application file for complete search history.

(56) References Cited

U.S. PATENT DOCUMENTS 5,147,902 A    9/1992  Ichikawa et al.
6,242,551 B1   6/2001  Tsuzuki et al.
(Continued)

FOREIGN PATENT DOCUMENTS

JP    2-232056    *  9/1990   ........... C09B 62/008
JP    02-232056 A    9/1990
(Continued)

OTHER PUBLICATIONS

International Search Report for International Application No. PCT/JP2013/062537, mailed on Jul. 30, 2013.
(Continued)

*Primary Examiner* — Ling Choi
*Assistant Examiner* — Chun-Cheng Wang
(74) *Attorney, Agent, or Firm* — Knobbe, Martens, Olson & Bear, LLP

(57) ABSTRACT

A polymerizable UV-absorbing colorant monomer is provided, which is excellent in stability under alkaline conditions and which is available for a useful material polymer for an intraocular lens. A compound, which is represented by the following general formula (1), is used as a polymerizable UV-absorbing monomer available for a material polymer for an intraocular lens:

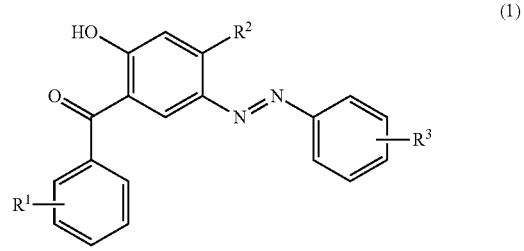

(in the general formula (1), $R^1$ is a hydrogen atom, a hydroxy group, a carboxy group, an alkyl group having 1 to 8 carbon atoms, an alkoxy group having 1 to 8 carbon atoms, a sulfonic acid group, or a benzyloxy group, $R^2$ is a hydrogen atom, a hydroxy group, or an alkoxy group having 1 to 4 carbon atoms, and $R^3$ is represented by the following formula (2)):

(in the general formula (2), $R^4$ is a hydrogen atom or a

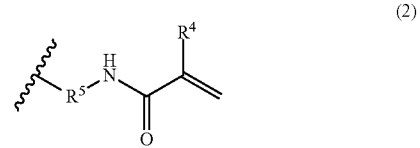

methyl group, and $R^5$ is a single bond or an alkylene group having 1 to 4 carbon atoms which may have a substituent or substituents.)

6 Claims, 2 Drawing Sheets

(56) References Cited

U.S. PATENT DOCUMENTS

| | | |
|---|---|---|
| 6,310,215 B1 | 10/2001 | Iwamoto |
| 2003/0077435 A1 | 4/2003 | Charkoudian et al. |
| 2008/0090937 A1 | 4/2008 | Jinkerson et al. |
| 2009/0082553 A1 | 3/2009 | Satake et al. |
| 2010/0065498 A1 | 3/2010 | Charkoudian et al. |
| 2010/0113641 A1 | 5/2010 | Laredo |
| 2011/0178202 A1 | 7/2011 | Laredo |
| 2012/0024787 A1 | 2/2012 | Charkoudian et al. |
| 2012/0288630 A1 | 11/2012 | Charkoudian et al. |

FOREIGN PATENT DOCUMENTS

| | | |
|---|---|---|
| JP | 05-88120 A | 4/1993 |
| JP | 07-28911 B2 | 4/1995 |
| JP | 2604799 B2 | 1/1997 |
| JP | 2012-508171 A | 4/2012 |
| WO | WO 03/008011 A1 | 1/2003 |
| WO | WO 2009/044853 A1 | 4/2009 |
| WO | WO 2009/044853 A1 | 9/2009 |

OTHER PUBLICATIONS

Office Action issued in the corresponding Chinese Application 2013800224114 dated May 28, 2015 with English translation.
Extended European Search Report issued in corresponding European Patent Application No. 13780703.8, dated Jan. 26, 2016.
Search Report and Written Opinion issued in corresponding Singapore application dated Oct. 1, 2015.
Office Action issued in corresponding JP Application No. 2014-512734, dated Apr. 26, 2016.

* cited by examiner

STABLE POLYMERIZABLE UV-ABSORBING COLORANT FOR INTRAOCULAR LENS

TECHNICAL FIELD

The present invention relates to a colorant for intraocular lenses. In particular, the present invention relates to a polymerizable colorant having an ability to absorb the ultraviolet light (UV) and the light in the blue region.

BACKGROUND ART

Cataract is a disease in which the opacity and the pigmentation arise in the crystalline lens to thereby cause a state that the entire visual field is fogged. As for the treatment method therefor, a surgical operation is generally performed such that the clouded crystalline lens is removed and an intraocular lens (IOL) is inserted into and installed in the capsule of crystalline lens. Most of the materials for the intraocular lens, which are used for the treatment, are based on acrylic or silicon polymer. In particular, for example, polymethyl methacrylate (PMMA) has been hitherto used.

However, the intrinsic crystalline lens has a property that the ultraviolet light is not transmitted therethrough. On the contrary, the ultraviolet light is transmitted through the conventional polymer for the intraocular lens. Therefore, there is a risk that the retina may be damaged.

Further, the intrinsic crystalline lens is slightly yellowish, which has a property that a part of the light in the blue region is suppressed from being transmitted. However, the light in the blue region is approximately completely transmitted through the conventional transparent polymer for the intraocular lens. Therefore, the patients complain the glare in many cases after the operation for inserting the intraocular lenses. Further, there has been also a risk that any disease originating from the retina including, for example, macular degeneration may be caused when the light in the blue region, which has the short wavelength and the high energy, arrives at the interior of the eye.

In view of the above, the material for the intraocular lens is required to have the ability to absorb the ultraviolet light and the coloring brought about by a yellow-based colorant. In recent years, in view of the safety, an UV absorber monomer and/or a yellow-based colorant monomer is/are copolymerized in many polymers for the intraocular lens. Various monomer compounds as described above have been hitherto developed (Patent Documents 1 to 4). Monomer compounds, which are copolymerizable with other monomers for the intraocular lens material, have been also developed, each of which has a chromophore such as an azo group or the like and a UV-absorbing portion such as a benzophenone skeleton or the like in one molecule (Patent Documents 5 and 6).

PRIOR ART DOCUMENTS

Patent Documents

Patent Document 1: JP2685980B2;
Patent Document 2: JPH10-251537A;
Patent Document 3: JPH07-028911B2;
Patent Document 4: JP2604799B2;
Patent Document 5: JPH02-232056A;
Patent Document 6: JP2006-291006A.

SUMMARY OF THE INVENTION

Problems to be Solved by the Invention

The polymerizable UV-absorbing colorant monomers described in Patent Documents 5 and 6 involve the following problem. That is, the monomers are deficient in the stability against the pH change, especially in the stability under alkaline conditions, and the colorant moiety (chromophore and UV-absorbing portion) is easily eliminated from the polymer. In particular, in the case of the intraocular lens material which is to be implanted in the eye for a long period of time, the risk of the elimination of the colorant moiety is further increased. In view of the above, an object of the present invention is to obtain a polymerizable UV-absorbing colorant monomer which is stable even under alkaline conditions.

Means for Solving the Problems

The present inventors have made diligent investigations in order to solve the problem as described above. As a result, it has been found out that the problem of the stability against the pH change is caused by the presence of any ester bond between a colorant moiety and a polymerizable group in a monomer. Further, it has been found out that a polymerizable UV-absorbing colorant monomer compound represented by the following general formula (1) can solve the problem as described above.

That is, the present invention is as follows.

One aspect of the present invention resides in a compound represented by the following general formula (1) (hereinafter referred to as "colorant compound of the present invention" as well).

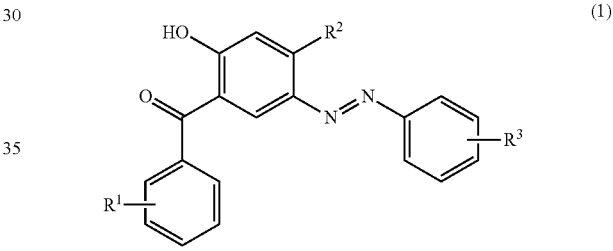

(In the general formula (1), $R^1$ is a hydrogen atom, a hydroxy group, a carboxy group, an alkyl group having 1 to 8 carbon atoms, an alkoxy group having 1 to 8 carbon atoms, a sulfonic acid group, or a benzyloxy group, and preferably a hydrogen atom, a methyl group, or an ethyl group. $R^2$ is a hydrogen atom, a hydroxy group, or an alkoxy group having 1 to 4 carbon atoms, and preferably a hydrogen atom, a hydroxy group, a methoxy group, or an ethoxy group. $R^3$ is represented by the following formula (2).)

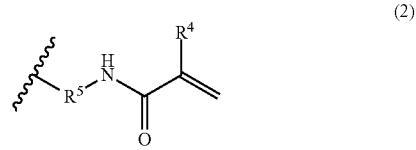

(In the general formula (2), $R^4$ is a hydrogen atom or a methyl group. Further, $R^5$ is a single bond or an alkylene group having 1 to 4 carbon atoms which may have a substituent or substituents, preferably an alkylene group having 1 to 4 carbon atoms which has no substituent.)

Another aspect of the present invention resides in a polymer (hereinafter referred to as "polymer of the present invention" as well) comprising the colorant compound of the present invention described above and one species or two or more species of other polymerizable monomers which are copolymerized with each other.

Still another aspect of the present invention resides in an intraocular lens (hereinafter referred to as "intraocular lens of the present invention" as well) comprising the polymer of the present invention described above which is molded.

Effect of the Invention

According to the present invention, the polymerizable UV-absorbing colorant monomer, which is stable even under alkaline conditions, is provided. The compound, which is represented by the general formula (1), has, in its molecule, the benzophenone skeleton which has the capability to absorb the ultraviolet light, the azobenzene skeleton which has the capability to absorb the light in the blue region, and the polymerizable group. Therefore, the compound represented by the general formula (1) can be copolymerized with another polymerizable monomer or polymerizable monomers to obtain a polymer. The polymer is useful as a material for the intraocular lens.

MODE FOR CARRYING OUT THE INVENTION

Figure 1:
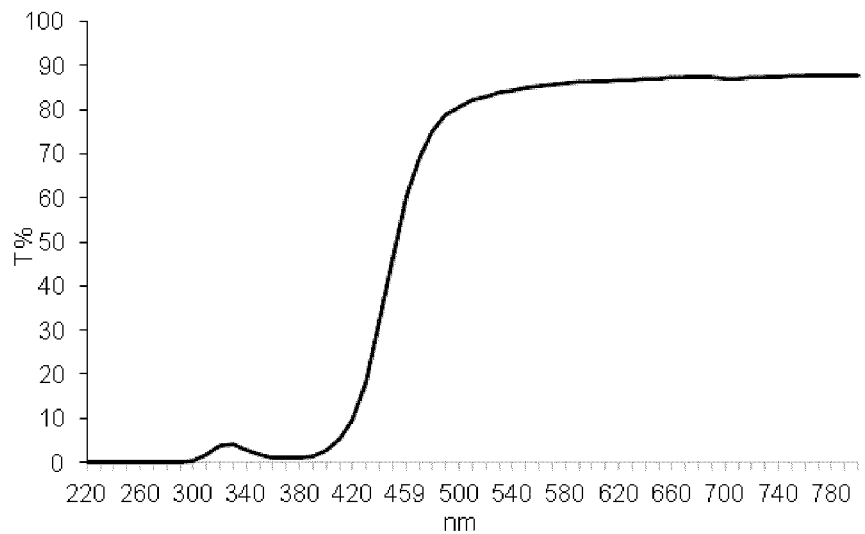
FIG. 1 shows a chart illustrating a UV-visible absorption spectrum of a polymer sheet obtained in Example 13.

The present invention will be explained in detail below.
<1> Colorant Compound of the Present Invention
The colorant compound of the present invention is represented by the following general formula (1).

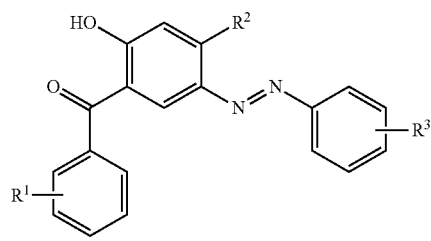
(1)

In the general formula (1), $R^1$ is a hydrogen atom, a hydroxy group, a carboxy group, an alkyl group having 1 to 8 carbon atoms, an alkoxy group having 1 to 8 carbon atoms, a sulfonic acid group, or a benzyloxy group. Among them, it is preferable to use the hydrogen atom, a methyl group, or an ethyl group in view of the reaction efficiency in the production. In the general formula (1), $R^2$ is a hydrogen atom, a hydroxy group, or an alkoxy group having 1 to 4 carbon atoms. Among them, it is preferable to use the hydrogen atom, the hydroxy group, a methoxy group, or an ethoxy group in view of the reaction efficiency in the production, and it is especially preferable to use the hydroxy group in view of the light beam absorption characteristic. As shown in the general formula (1), the colorant compound of the present invention has the benzophenone skeleton and the azobenzene skeleton, and they are the colorant moieties. In the general formula (1), $R^3$ is represented by the following formula (2).

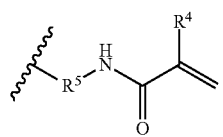
(2)

In the general formula (2), $R^4$ is a hydrogen atom or a methyl group.
In the general formula (2), $R^5$ is a single bond or an alkylene group having 1 to 4 carbon atoms which may have a substituent or substituents, preferably an alkylene group having 1 to 4 carbon atoms which has no substituent. The alkylene group having 1 to 4 carbon atoms specifically means a methylene group, an ethylene group, a propylene group, or a butylene group. The alkylene group as described above may have a substituent or substituents, or the alkylene group as described above may have no substituent. When the alkylene group as described above has a substituent or substituents, it is possible to exemplify such a mode that a substituent or substituents including, for example, an alkyl group having 1 to 2 carbon atoms, a halogen group, a carboxyl group, a carboxy-C1 to C2-alkyl group, a hydroxy group, a hydroxy-alkyl group having 1 to 2 carbon atoms, an amino group, and an aminoalkyl group having 1 to 2 carbon atoms is/are bonded to a carbon atom or atoms of the alkylene group.

As described above, the substituent $R^3$ is the group in which the spacer is bonded to the (meth)acryloylamino group which is the polymerizable group, and the substituent $R^3$ is the moiety which participates in the copolymerization in the colorant compound of the present invention. Owing to the structure represented by the general formula (2), the colorant compound of the present invention has a property that the reaction efficiency is high with respect to other polymerizable monomers.

The term "(meth)acryloyl" means "acryloyl" or "methacryloyl".

In the general formula (1), it is preferable that the substituent $R^3$ is bonded to the 3-position or the 4-position of the azophenyl group.

The colorant compound of the present invention represented by the general formula (1) is not particularly limited, for example, those having the following structure may be preferably exemplified.

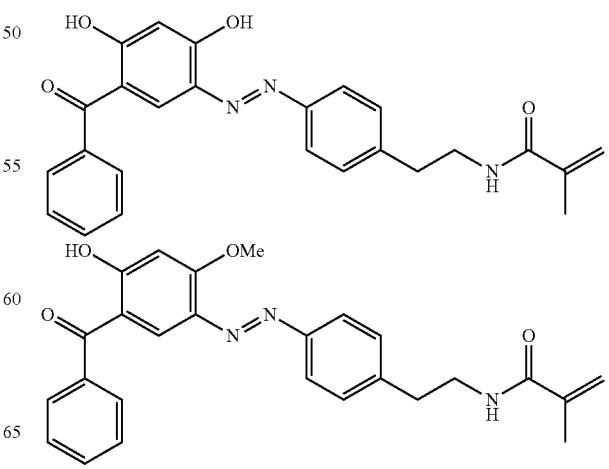

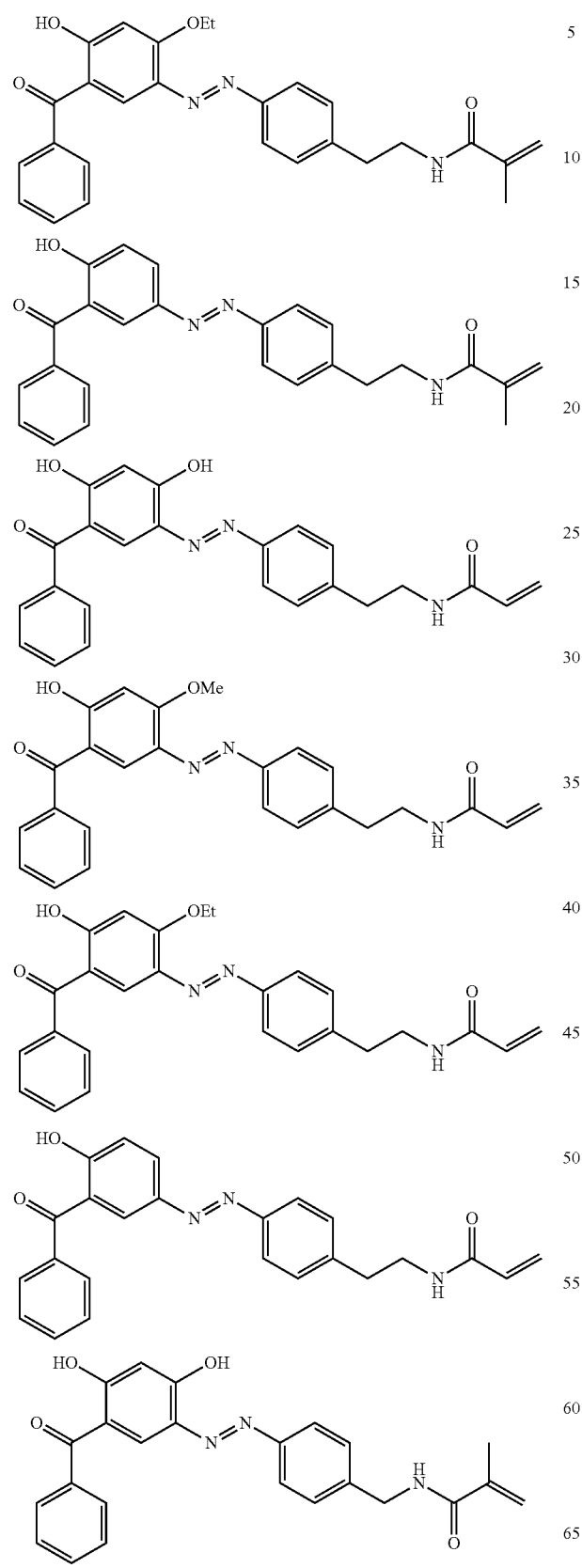
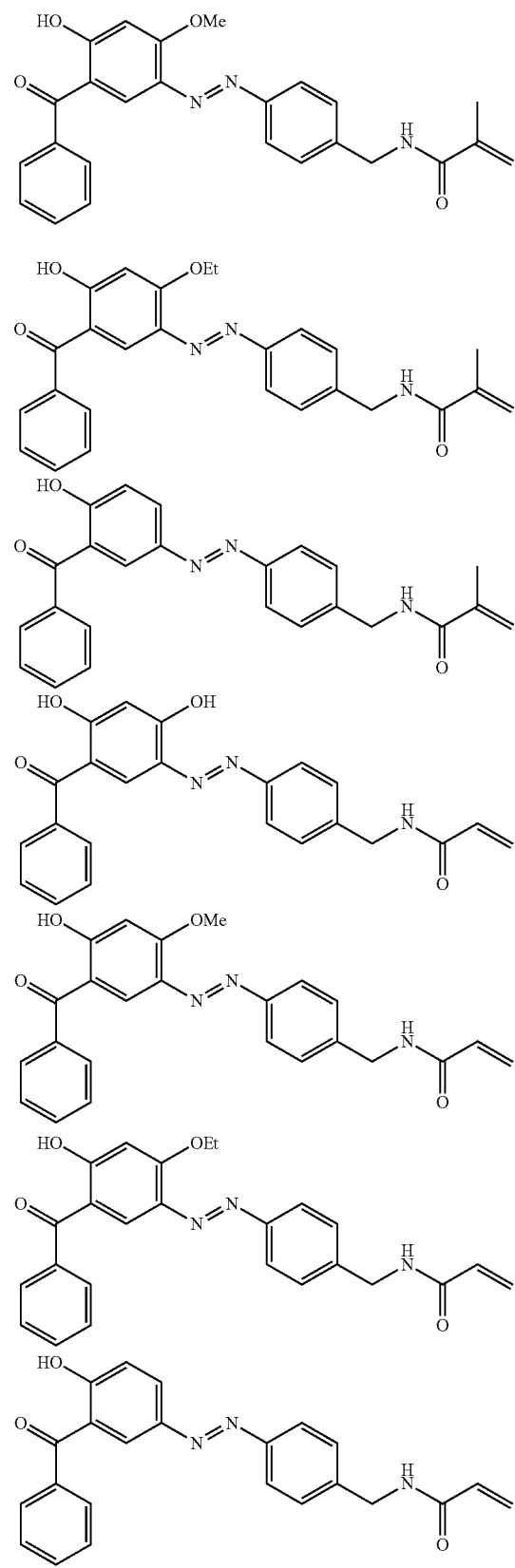

The colorant compound of the present invention has, in one molecule, the benzophenone skeleton (UV-absorbing portion) which has the capability to absorb the ultraviolet light and the azobenzene skeleton (chromophore) which has the capability to absorb the light in the blue region. Owing to the presence of the colorant moiety of them, the colorant compound of the present invention has the capability (light beam absorption characteristic) to suppress the transmission of those in the UV region (wavelength: not more than 380 nm) and the blue region (wavelength: 380 to 500 nm). The colorant compound of the present invention is more excellent in the light beam absorption characteristic as compared with any conventional colorant compound (for example, 2,4-dihydroxy-5-(4-(2-(N-2-methacryloyloxyethyl)carbamoyloxy) ethylphenylazo)benzophenone (BMAC) described in Patent Document 6. Specifically, when the UV-visible absorption spectrum is measured, the rising of the chart sharply appears in the vicinity of 420 to 500 nm, and the compound is excellent in the ability to suppress the light beam transmission in the UV/blue region.

Further, as for the colorant compound of the present invention, the UV-absorbing portion and the chromophore (collectively referred to as "colorant moiety" as well) exist in one molecule. Therefore, the inconvenience, in which the chromophore is damaged by the ultraviolet light and the colorant is subjected to the discoloration in a time-dependent manner, is scarcely caused.

Additionally, the polymerizable group and the colorant moiety are connected by the amide bond in the colorant compound of the present invention. The bond as described above is stable even under the alkaline conditions, and hence the colorant moiety is not eliminated from the polymer of the present invention as described later on. As a result, the stability under the alkaline conditions is realized, which has been deficient in any conventional colorant compound having the ester bond and any copolymer based on the use of the same.

The method for producing the colorant compound of the present invention is not specifically limited. However, for example, the colorant compound of the present invention can be produced in accordance with Synthesis Methods 1 to 3 described below.

(Synthesis Method 1)

This method includes a diazotization step of an aminoaryl compound to obtain a diazonium salt, a diazo coupling step of the obtained diazonium salt and a benzophenone compound to give a diazo compound, and an amidation step of reacting the resulting diazo compound, for example, with an acrylic acid compound or a methacrylic acid compound by means of an amidation reaction to introduce a polymerizable group.

The outline of Synthesis Method 1 is shown in the following reaction formula. In the formula, R represents a protecting group, R' represents a hydroxy group or a halogen atom, and $R^1$ to $R^5$ represent the same or equivalent substituents as those described above.

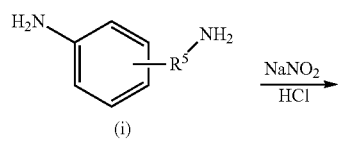

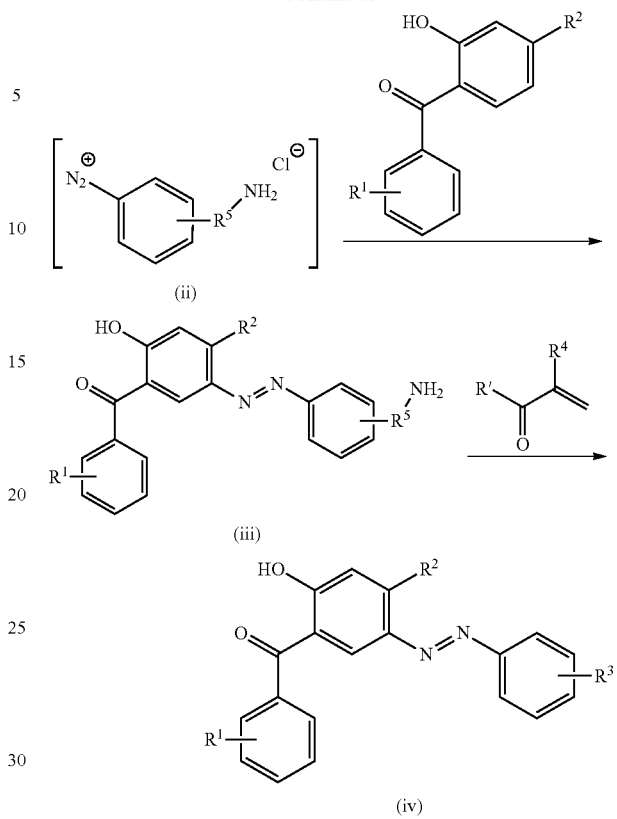

(Synthesis Method 2)

This method includes an amidation step of an aminoaryl compound, for example, with an acrylic acid compound or a methacrylic acid compound by means of an amidation reaction to introduce a polymerizable group, a diazotization step of the obtained polymerizable aminoaryl compound to give a diazonium salt, and a diazo coupling step of performing diazo coupling of the resulting diazonium salt with a benzophenone compound to give the colorant compound of the present invention.

The outline of Synthesis Method 2 is shown in the following reaction formula. In the formula, R represents a protecting group, R' represents a hydroxy group or a halogen atom, and $R^1$ to $R^5$ represent the same or equivalent substituents as those described above.

In the amidation step of introducing the polymerizable group into the aminoaryl compound, it is preferable that the amino group on the aromatic group is blocked by the protecting group is used, and the protecting group is removed, for example, by means of an acid treatment before the diazotization step.

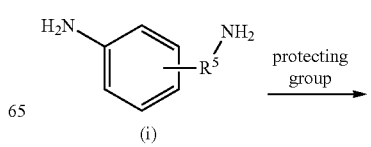

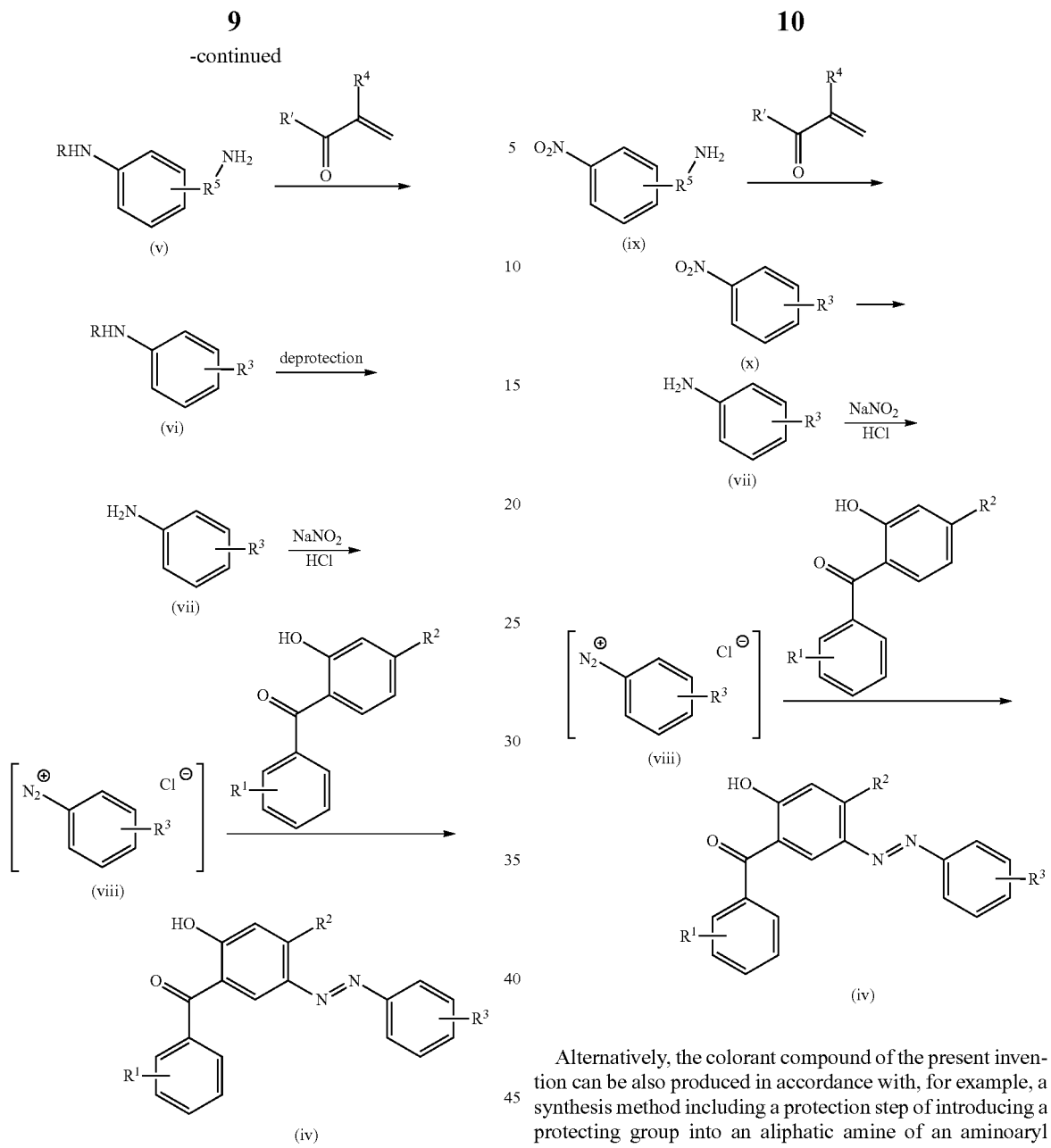

(Synthesis Method 3)

This method includes an amidation step of using a nitroaryl compound as a starting material in place of the aminoaryl compound and reacting it, for example, with an acrylic acid compound or a methacrylic acid compound by means of an amidation reaction to introduce a polymerizable group, a reducing step of a nitro group of the obtained polymerizable nitroaryl compound to an amino group, a diazotization step of the obtained polymerizable aminoaryl compound to give a diazonium salt, and a diazo coupling step of the resulting diazonium salt with a benzophenone compound to give the colorant compound of the present invention.

The outline of Synthesis Method 3 is shown in the following reaction formula. In the formula, R' represents a hydroxy group or a halogen atom, and $R^1$ to $R^5$ represent the same or equivalent substituents as those described above.

Alternatively, the colorant compound of the present invention can be also produced in accordance with, for example, a synthesis method including a protection step of introducing a protecting group into an aliphatic amine of an aminoaryl compound, a diazotization step of the aminoaryl compound in which the aliphatic amine is protected to obtain a diazonium salt, a diazo coupling step of the resulting diazonium salt with a benzophenone compound to give a diazo compound, a deprotection step of removing the protecting group of the aliphatic amine, for example, by means of an acid treatment, and an amidation step of reacting the resulting diazo compound, for example, with an acrylic acid compound or a methacrylic acid compound by means of an amidation reaction to introduce a polymerizable group.

The diazotization step, which is included in the respective synthesis methods described above, can be carried out in accordance with any known method.

It is possible to use, for example, as the diazotizing agent, sodium nitrite or aqueous solution of sodium nitrite, potassium nitrite or aqueous solution of potassium nitrite, isoamyl nitrite, and/or nitrosyl sulfate (sulfuric acid solution). The amount of use of the diazotizing agent is not specifically limited. However, the amount of use of the diazotizing agent is preferably 1.00 to 1.20 moles and more preferably 1.02 to 1.10 moles per 1 mole of the polymerizable group-containing aminoaryl compound. The reaction temperature in the diazotization step is within a range of −78° C. to 50° C. The reaction temperature is preferably within a range of −20° C. to 20° C. and more preferably within a range of −20° C. to 10° C. It is preferable that the diazotization step is performed under a neutral to acidic condition. It is possible to appropriately add acid such as hydrochloric acid or the like to the reaction solvent.

It is preferable that the diazo coupling step, which is included in Synthesis Methods 2 and 3, is performed under a weakly basic condition by using a weak base as a catalyst, for the following reason. That is, in the case of the strong base including, for example, sodium hydroxide and potassium hydroxide generally used in the diazo coupling reaction, the amide structure, which is included in the diazonium salt of the polymerizable aminoaryl compound, is decomposed or eliminated, and the yield of the objective compound is lowered. On the contrary, when the weak base is used, then the decomposition can be remarkably suppressed, and it is possible to secure the sufficient reactivity. As a result, it is possible to dramatically raise the reaction yield. Further, it is known that the vinyl group, which is included in the diazonium salt, is also polymerized in the presence of the strong base as described above, which causes the conspicuous decrease in the yield. However, when the weak base is used in place of the strong base, it is also possible to suppress such an inconvenience.

The weak base, which is usable in this procedure, is not specifically limited provided that the weak base is a salt composed of a strong alkali and a weak acid, wherein an aqueous solution thereof does not hydrolyze the amide bond at 1 atm at 0° C. to 25° C., causing no polymerization reaction of the vinyl group. It is preferable to use a weak base including, for example, sodium carbonate, sodium hydrogencarbonate, potassium carbonate, sodium acetate, and potassium acetate. The amount of use of the weak base is preferably 4.0 to 10.0 moles and more preferably 6.0 to 8.0 moles per 1 mole of diazonium salt as converted into the sodium equivalent. Further, the reaction temperature in the diazo coupling step is within a range of −10° C. to 10° C. and more preferably within a range of −5° C. to 5° C.

It is possible to use, as the reaction solvent in the diazo coupling step, organic solvents (alcohol-based solvent such as methanol, ethanol, isopropyl alcohol and the like, amide-based solvent such as N,N-dimethylacetoamide, N,N-dimethylformamide, 1-methyl-2-pyrrolidone and the like, sulfon-based solvent such as sulforan and the like, sulfoxide-based solvent such as dimethyl sulfoxide and the like, ureide-based solvent such as tetramethylurea and the like, halogen-based solvent such as dichloromethane, chloroform, 1,2-dichloroethane and the like, ester-based solvent such as ethyl acetate, butyl acetate and the like, ether-based solvent such as diethyl ether, tetrahydrofuran and the like, and pyridine-based solvent such as pyridine, α-picoline, 2,6-lutidine and the like) singly or as a mixture system composed of a plurality of types, as well as a mixture system composed of the organic solvent and water and a system composed of water singly. However, among them, it is preferable to use the alcohol-based solvent. Further, it is also preferable to use the above while mixing the same with water. Further, it is also allowable to add and use the amide-based solvent, the ester-based solvent, and/or the ether-based solvent in addition to the alcohol-based solvent and the water depending on the reaction.

The aminoaryl compound referred to herein is represented by (i) or (v) in the reaction formula described above, and the nitroaryl compound is represented by (ix) in the same. Further, the polymerizable aminoaryl compound is represented by (vi) or (vii) in the reaction formula described above, and the polymerizable nitroaryl compound is represented by (x) in the same.

The polymerizable aminoaryl compound or the polymerizable nitroaryl compound described above can be obtained, for example, by the amidation reaction of amino-substituted aromatic amine or nitro-substituted aromatic amine and (meth)acrylic acid, the amidation reaction of amino-substituted aromatic alkylamine or nitro-substituted aromatic alkylamine and (meth)acrylic acid, the amidation reaction of amino-substituted aromatic amine or nitro-substituted aromatic amine and (meth)acrylic acid chloride, or the amidation reaction of amino-substituted aromatic alkylamine or nitro-substituted aromatic alkylamine and (meth)acrylic acid chloride. As for the amino-substituted aromatic compound, it is possible to use those in which the amide group is substituted with a protecting group including, for example, t-butoxycarbonyl group, benzyloxycarbonyl group, 9-fluorenylmethyloxycarbonyl group, 2,2,2-trichloroethoxycarbonyl group, allyloxycarbonyl group, p-toluenesulfonyl group, and 2-nitrobenzenesulfonyl group.

The polymerizable aminoaryl compound described above is exemplified, for example, by N-(4-aminophenyl) (meth)acrylamide, N-[(4-aminophenyl)methyl](meth)acrylamide, N-[2-(4-aminophenyl)ethyl](meth)acrylamide, N-[3-(4-aminophenyl)propyl](meth)acrylamide, N-[4-(4-aminophenyl)butyl](meth)acrylamide, N-[(3-aminophenyl)methyl](meth)acrylamide, N-[2-(3-aminophenyl)ethyl](meth)acrylamide, N-[3-(3-aminophenyl)propyl](meth)acrylamide, and N-[4-(3-aminophenyl)butyl](meth)acrylamide.

Further, the polymerizable nitroaryl compound described above is exemplified, for example, by N-(4-nitrophenyl)(meth)acrylamide, N-[(4-nitrophenyl)methyl](meth)acrylamide, N-[2-(4-nitrophenyl)ethyl](meth)acrylamide, N-[3-(4-nitrophenyl)propyl](meth)acrylamide, N-[4-(4-nitrophenyl)butyl](meth)acrylamide, N-[(3-nitrophenyl)methyl](meth)acrylamide, N-[2-(3-nitrophenyl)ethyl](meth)acrylamide, N-[3-(3-nitrophenyl)propyl](meth)acrylamide, and N-[4-(3-nitrophenyl)butyl](meth)acrylamide.

As for the production method for producing the colorant compound of the present invention, it is preferable to use the synthesis method in which the amidation step is performed before the diazo coupling step as in Synthesis Method 2 or Synthesis Method 3, for the following reason. That is, in the diazotization step of Synthesis Method 1 described above, it is feared that any byproduct having the high reactively may be produced by the diazotization of aromatic amine. On the contrary, according to Synthesis Method 2 or Synthesis Method 3 described above, the diazotization step is performed after previously introducing the polymerizable group by means of, for example, the amidation reaction. Therefore, it is possible to avoid the production of the byproduct as described above. As a result, according to Synthesis Method 2 or Synthesis Method 3, the reaction efficiency is satisfactory, and it is possible to obtain the colorant compound of the present invention at a high yield.

Further, the nitroaryl compound, which is used as the starting material in Synthesis Method 3, is more inexpensive than the aminoaryl compound. Additionally, in the amidation reaction, a byproduct, in which two molecules of the polymerizable groups are introduced with respect to the amino group, is usually produced when the polymerizable group is introduced. However, the byproduct, which is produced when the nitroaryl compound is amidated, is removed more easily than that produced, for example, when the aminoaryl compound is amidated. Therefore, taking the economy and the convenience of the operation into consideration as well, Synthesis Method 3, in which the nitroaryl compound is used as the starting material, is especially preferred as the production method for producing the colorant compound of the present invention. The colorant compound of the present invention can be industrially produced by producing the same in accordance with Synthesis Method 2 or Synthesis Method 3. The colorant compound of the present invention is usable as a useful colorant or a polymerizable UV-absorbing colorant monomer.

<2> Polymer of the Present Invention

The colorant compound of the present invention can be made into a polymer by copolymerizing the colorant compound of the present invention with one species or two or more species of other copolymerizable monomer or monomers. In the colorant compound of the present invention, the chromophore and the polymerizable group are sterically separated from each other, and hence the polymerization is not inhibited. Therefore, the colorant compound of the present invention can be used as a copolymerizable monomer which has the satisfactory reactivity with respect to other copolymerizable monomers. Other copolymerizable monomers as described above are not specifically limited provided that the monomers are ordinarily used. However, for example, the following monomers are exemplified.

Straight-chain, branched-chain, and cyclic alkyl(meth)acrylates including, for example, methyl (meth)acrylate, ethyl (meth)acrylate, propyl (meth)acrylate, isopropyl (meth)acrylate, butyl (meth)acrylate, tert-butyl (meth)acrylate, isobutyl (meth)acrylate, pentyl (meth)acrylate, tert-pentyl (meth)acrylate, hexyl (meth)acrylate, heptyl (meth)acrylate, octyl (meth)acrylate, 2-ethylhexyl (meth)acrylate, nonyl (meth)acrylate, decyl (meth)acrylate, dodecyl (meth)acrylate, stearyl (meth)acrylate, cyclopentyl (meth)acrylate, cyclohexyl (meth)acrylate, and phenoxy (meth)acrylate;

silicon-containing (meth)acrylates including, for example, pentamethyldisiloxanylmethyl (meth)acrylate, pentamethyldisiloxanylpropyl (meth)acrylate, methylbis(trimethylsiloxy)silylpropyl (meth)acrylate, tris(trimethylsiloxy)silylpropyl (meth)acrylate, mono(methylbis(trimethylsiloxy)siloxy)bis (trimethylsiloxy)-silylpropyl (meth)acrylate, tris(methylbis (trimethylsiloxy)siloxy)silylpropyl (meth)acrylate, methylbis(trimethylsiloxy)silylpropylglyceryl (meth)acrylate, tris (trimethylsiloxy)silylpropylglyceryl (meth)acrylate, mono (methylbis(trimethylsiloxy)siloxy)bis(trimethylsiloxy)-silylpropylglyceryl (meth)acrylate, trimethylsilylethyltetramethyldisiloxanylpropylglyceryl (meth)acrylate, trimethylsilylmethyl (meth)acrylate, trimethylsilylpropyl (meth)acrylate, trimethylsilylpropylglyceryl (meth)acrylate, pentamethyldisiloxanylpropylglyceryl (meth)acrylate, methylbis(trimethylsiloxy)silylethyltetramethyldisiloxanyl-methyl (meth)acrylate, tetramethyltriisopropylcyclotetrasiloxanylpropyl (meth)acrylate, and tetramethyltriisopropylcyclotetrasiloxybis(trimethyl-siloxy) silylpropyl (meth)acrylate;

fluorine-containing (meth)acrylates including, for example, trifluoroethyl (meth)acrylate, tetrafluoropropyl (meth)acrylate, pentafluoropropyl (meth)acrylate, hexafluoroisopropyl (meth)acrylate, tetrafluoro-tert-pentyl (meth) acrylate, hexafluorobutyl (meth)acrylate, hexafluoro-tert-hexyl (meth)acrylate, octafluoropentyl (meth)acrylate, 2,3,4, 5,5,5-hexafluoro-2,4-bis(trifluoromethyl)pentyl (meth) acrylate, dodecafluoroheptyl (meth)acrylate, 2-hydroxyoctafluoro-6-trifluoromethylheptyl (meth)acrylate, 2-hydroxydodecafluoro-8-trifluoromethylnonyl (meth) acrylate, and 2-hydroxyhexadecafluoro-10-trifluoromethylundecyl (meth)acrylate;

styrene derivatives including, for example, styrene, pentafluorostyrene, methylstyrene, trimethylstyrene, trifluoromethylstyrene, (pentamethyl-3,3-bis(trimethylsiloxy)trisiloxanyl)styrene, (hexamethyl-3-trimethylsiloxytrisiloxyanyl)styrene, and dimethylaminostyren;

hydroxy group-containing (meth)acrylates including, for example, hydroxyethyl (meth)acrylate, hydroxypropyl (meth)acrylate, hydroxybutyl (meth)acrylate, dihydroxypropyl (meth)acrylate, dihydroxydibutyl (meth)acrylate, diethylene glycol mono(meth)acrylate, triethylene glycol mono (meth)acrylate, and dipropylene glycol mono(meth)acrylate;

(meth)acrylic acid;

vinyl lactams including, for example, N-vinylpyrrolidone, α-methylene-N-methylpyrrolidone, N-vinylcaprolactam, and N-(meth)acryloylpyrrolidone;

(meth)acrylamides including, for example, (meth)acrylamide, N-methyl(meth)acrylamide, N-ethyl(meth)acrylamide, N-hydroxyethyl(meth)acrylamide, N,N-dimethyl (meth)acrylamide, N,N-diethyl(meth)acrylamide, and N-ethyl-N-aminoethyl(meth)acrylamide;

aminoalkyl(meth)acrylates including, for example, aminoethyl (meth)acrylate, N-methylaminoethyl (meth)acrylate, and N,N-dimethylaminoethyl (meth)acrylate;

alkoxy group-containing (meth)acrylates including, for example, methoxyethyl (meth)acrylate, ethoxyethyl (meth) acrylate, and methoxydiethylene glycol (meth)acrylate;

aromatic ring-containing (meth)acrylates including, for example, benzyl (meth)acrylate;

alkyl esters, which may be substituted with alkyl group, fluorine-containing alkyl group or siloxanylalkyl group, of itaconic acid, crotonic acid, maleic acid, fumaric acid and the like;

glycidyl (meth)acrylate;

tetrahydrofurfuryl (meth)acrylate;

4-vinylpyridine;

heterocyclic N-vinyl monomers including, for example, vinylimidazole, N-vinylpyperidone, N-vinylpiperidine, and N-vinylsuccinimide;

N-(meth)acryloylpiperidine; and

N-(meth)acryloylmorpholine.

The term "(meth)acrylate" means "acrylate" or "methacrylate", and this meaning also holds in the same manner in relation to (meth)acrylic acid derivatives.

One species or two or more species of the copolymerizable monomers described above can be selected and polymerized to provide a macromonomer which can be used as one of the copolymerizable monomers for producing the polymer as well.

The polymer of the present invention can be obtained by blending the colorant compound of the present invention and one species or two or more species of other copolymerizable monomers in arbitrary amounts, mixing them uniformly or homogeneously, and then copolymerizing them. The ratio, at which the colorant compound of the present invention is blended when the polymer of the present invention is copolymerized, is affected by the way of use of the polymer, for example, the thickness in the case of the intraocular lens as well. However, the ratio is preferably 0.001 to 5 parts by weight, more preferably 0.005 to 2 parts by weight, and much more preferably 0.01 to 0.06 parts by weight with respect to 100 parts by weight of the mixture of all of the copolymerizable monomers. If the ratio is less than 0.001 parts by weight, it is feared that the color development of the polymer may be deteriorated. On the other hand, if the ratio exceeds 5 parts by weight, it is feared that the transparency may be lowered due to the excessive denseness of the coloring of the polymer, the physical property (for example, the strength) of the polymer may be lowered, and/or the colorant compound of the present invention may be easily eluted from the polymer.

The polymer of the present invention can be synthesized in accordance with any method ordinarily carried out in the concerning technical field. For example, the polymerization can be performed by uniformly or homogeneously mixing the colorant compound of the present invention with one species or two or more species of other copolymerizable monomers, adding a polymerization initiator, if necessary, and gradually performing the heating within a temperature range of room temperature to about 130° C., or radiating an electromagnetic wave including, for example, a microwave, an ultraviolet light, and a radiation (gamma ray). As for the polymerization, it is possible to adopt various methods widely and generally used by those skilled in the art including, for example, the radical polymerization, the bulk polymerization, and the solvent polymerization (solution polymerization). When the heating polymerization is performed, it is also allowable that the temperature is raised in a stepwise manner.

The polymerization initiator described above is exemplified, for example, by radical polymerization initiators including, for example, azobisisobutyronitrile, azobisdimethylvaleronitrile, 2,2'-azobis(2,4-dimethylvaleronitrile), benzoyl peroxide, tert-butyl hydroperoxide, cumene hydroperoxide, and benzoyl peroxide. It is possible to use one species or two or more species of them. It is preferable that the polymerization initiator is used in an amount of use within a range of about 0.01 to 1 part by weight with respect to 100 parts by weight of the mixture of all of the copolymerizable monomers. When the polymerization is performed by using the light beam (ray) or the like, it is preferable to further add a photoinitiator (photopolymerization initiator) and a sensitizer.

When the polymer of the present invention is synthesized, it is also possible to use, in combination, a known polymerizable UV absorber (ultraviolet absorber or absorbent) (to mainly absorb the ultraviolet light portion) and a polymerizable colorant (having no UV-absorbing capability to mainly absorb the light in the blue region) as well as a polymerizable UV-absorbing colorant. When the polymerizable UV absorber, the polymerizable colorant, and the polymerizable UV-absorbing colorant as described above are used in combination, it is thereby possible to finely adjust the balance between the UV-absorbing capability and the absorbing capability to absorb the light in the blue region of the polymer to be finally obtained. In particular, when the polymer of the present invention is used as a material for the intraocular lens as described later on, the use in combination as described above is useful in order to adjust the color tone of the intraocular lens and/or sufficiently add the UV-absorbing ability. The adjustment is made so that the amount of addition is preferably not less than 0.01 parts by weight and more preferably not less than 0.05 parts by weight with respect to 100 parts by weight of the mixture of all of the copolymerizable monomers. Further, in order to secure the sufficient polymerization speed and the sufficient degree of polymerization, the adjustment is made so that the amount of addition is preferably not more than 5 parts by weight and more preferably not more than 3 parts by weight with respect to 100 parts by weight of the mixture of all of the copolymerizable monomers.

As for the polymerizable UV absorber capable of being used in combination for the purpose as described above, it is possible to use, for example, benzophenone-based polymerizable UV absorbers disclosed in Japanese Patent Application Laid-open No. 2003-253248 and benzotriazole-based polymerizable UV absorbers disclosed in Japanese Patent No. 2685980. Specified examples are exemplified, for example, by benzophenone-based polymerizable UV absorbers including, for example, 2-hydroxy-4-(meth)acryloyloxybenzophenone, 2-hydroxy-4-(meth)acryloyloxy-5-t-butylbenzophenone, 2-hydroxy-4-(meth)acryloyloxy-2',4'-dichlorobenzophenone, and 2-hydroxy-4-(2'-hydroxy-3'-(meth)acryloyloxypropoxy)benzophenone; benzotriazole-based polymerizable UV absorbers including, for example, 2-(2'-hydroxy-5'-(meth)acryloyloxyethylphenyl)-2H-benzotriazole, 2-(2'-hydroxy-5'-(meth)acryloyloxyethylphenyl)-5-chloro-2H-benzotriazole, 2-(2'-hydroxy-5'-(meth)acryloyloxypropylphenyl)-2H-benzotriazole, 2-(2'-hydroxy-5'-(meth)acryloyloxypropyl-3'-t-butylphenyl)-5-chloro-2H-benzotriazole, and 2-(2'-hydroxy-5'-(2''-methacryloyloxyethoxy)-3'-t-butylphenyl)-5-methyl-2H-benzotriazole; salicylic acid derivative-based polymerizable UV absorber including, for example, 2-hydroxy-4-methacryloyloxymethylbenzoic acid phenylester; and 2-cyano-3-phenyl-3-(3'-(meth)acryloyloxyphenyl)propenic acid methylester. These compounds can be used singly, or two or more species of these compounds can be used in mixture.

As for the polymerizable colorant which can be used in combination for the purpose as described above, it is possible to use, for example, azo-based, anthraquinone-based, nitro-based, and phthalocyanine-based polymerizable colorants disclosed in Japanese Patent Application Laid-open No. 10-251537. These colorants can be used singly, or two or more species of these colorants can be used in mixture.

Specified examples of the polymerizable azo-based colorant are exemplified, for example, by 1-phenylazo-4-(meth)acryloyloxynaphthalene, 1-phenylazo-2-hydroxy-3-(meth)acryloyloxynaphthalene, 1-naphtylazo-2-hydroxy-3-(meth)acryloyloxynaphthalene, 1-(α-anthrylazo-2-hydroxy-3-(meth)acryloyloxynaphthalene, 1-((4'-(phenylazo) -phenyl) azo)-2-hycrosy-3-(meth)acryloyloxynaphthalene, 1-(2',4'-xylylazo)-2-(meth)acryloyloxynaphthalene, and 1-(o-tolylazo)-2-(meth)acryloyloxynaphthalene, 2-(m -(meth)acryloylamide-anilino)-4,6-bis(1'-(o-tolylazo)-2'-naphthylamino)-1,3,5-triazine, 2-(m-vinylanilino)-4-(4'-nitrophenylazo)-anilino)-6-chloro-1,3,5-triazine, 2-(1'-(o -tolylazo)-2'-naphthyloxy)-4-(m-vinylanilino)-6-chloro -1,3,5-triazine, 2-(p-vinylanilino)-4-(1'-(o-tolylazo)-2'-naphthylamino)-6-chloro-1,3,5-triazine, N-(1'-(o-tolylazo) -2'-naphtyhl)-3-vinylphthalic acid monoamide, N-(1'-(o -tolylazo)-2'-naphtyl)-6-vinylphthalic acid monoamide, 3-vinylphthalic acid-(4'-(p-sulfonylazo)-1'-naphthyl) monoester and 6-vinylphthalic acid-(4'-(p-sulfonylazo)-1'-naphthyl) monoester, 3-(meth)acryloylamide-4-phenylazophenol, 3-(meth)acryloylamide-4-(8'-hydroxy-3',6'-disulfo-1'-naphthylazo)-phenol, 3-(meth)acryloylamide-4-(1'-phenylazo-2'-naphthylazo)-phenol, 3-(meth)acryloylamide-4-(p-tolylazo)phenol, 2-amino-4-(m-(2'-hydroxy-1'-naphthylazo)anilino)-6-isopropenyl-1,3,5-triazine, 2-amino-4-(N-methyl-p-(2'-hydroxy-1'-naphthylazo)anilino)-6-isopropenyl-1,3,5-triazine, 2-amino -4-(m-(4'-hydroxy-1'-phenylazo)anilino)-6-isopropenyl-1,3,5-triazine, 2-amino-4-(N-methyl-p-(4'-hydroxyphenylazo)anilino)-6-isopropenyl-1,3,5-triazine, 2-amino-4-(m-(3'-methyl-1'-phenyl-5'-hydroxy-4'-pyrazolylazo) anilino)-6-isopropenyl-1,3,5-triazine, 2-amino-4-(N-methyl-p-(3'-methyl-1'-phenyl-5'-hydroxy-4'-pyrazolylazo) anilino)-6-isopropenyl-1,3,5-triazine, 2-amino-4-(p-phenylazoanilino)-6-isopropenyl-1,3,5-triazine, and 4-phenylazo-7-(meth)acryloylamide-1-naphthol.

Specified examples of the polymerizable anthraquinone-based colorant are exemplified, for example, by 1,5-bis ((meth)acryloylamino)-9,10-anthraquinone, 1-(4'-vinylbenzoylamide)-9,10-anthraquinone, 4-amino-1-(4'- vinylbenzoylamide)-9,10-anthraquinone, 5-amino-1-(4'-vinylbenzoylamide)-9,10-anthraquinone, 8-amino-1-(4'-vinylbenzoylamide)-9,10-anthraquinone, 4-nitro-1-(4'-vinylbenzoylamide)-9,10-anthraquinone, 4-hydroxy-1-(4'-vinylbenzoylamide)-9,10-anthraquinone, 1-(3'-vinylbenzoylamide)-9,10-anthraquinone, 1-(2'-vinylbenzoylamide)-9,10-anthraquinone, 1-(4'-isopropenylbenzoylamide)-9,10-anthraquinone, 1-(3'-isopropenylbenzoylamide)-9,10-anthraquinone, 1-(2'-isopropenylbenzoylamide)-9,10-anthraquinone, 1,4-bis(4'-vinylbenzoylamide)-9,10-anthraquinone, 1,4-bis(4'-isopropenylbenzoylamide)-9,10-anthraquinone, 1,5'-bis(4'-vinylbenzoylamide)-9,10-anthraquinone, 1,5-bis(4'-isopropenylbenzoylamide)-9,10-anthraquinone, 1-methylamino -4-(3'-vinylbenzoylamide)-9,10-anthraquinone, 1-methylamino -4-(4'-vinylbenzoyloxyethylamino)-9,10-anthraquinone, 1-amino-4-(3'-vinylphenylamino)-9,10-anthraquinone-2-sulfonic acid, 1-amino-4-(4'-vinylphenylamino)-9,10-anthraquinone-2-sulfonic acid, 1-amino-4-(2'-vinylbenzylamino)-9,10-anthraquinone-2-sulfonic acid, 1-amino-4-(3'-(meth)acryloylaminophenylamino)-9,10-anthraquinone-2-sulfonic acid, 1-amino-4-(3'-(meth)acryloylaminobenzylamino)-9,10-anthraquinone-2-sulfonic acid, 1-(β-ethoxycarbonylallylamino)-9,10-anthraquinone, 1-(β-carboxyallylamino)-9,10-anthraquinone, 1,5-di-(β-carboxyallylamino)-9,10-anthraquinone, 1-(β-isopropoxycarbonylallylamino)-5-benzoylamide-9,10-anthraquinone, 2-(3'-(meth)acryloylamide-anilino)-4-(3'-(3"-sulfo-4"-aminoanthraquinone-1"-yl)-amino-anilino)-6-chloro-1,3,5-triazine, 2-(3'-(meth)acryloylamide-anilino) -4-(3'-(3"-sulfo-4"-aminoanthraquinone-1"-yl)-amino -anilino)-6-hydrzino-1,3,5-triazine, 2,4-bis-((4"-methoxyanthraquinonen-1"-yl)-amino)-6-(3'-vinylanilino) -1,3,5-triazine, and 2-(2'-vinylphenoxy)-4-(4'-(3"-sulfo-4"-aminoanthraquinone-1"-yl-amino)-anilino)-6-chloro-1,3,5-triazine.

Specified examples of the polymerizable nitro-based colorant are exemplified, for example, by o-nitroanilinomethyl (meth)acrylate.

Specified examples of the polymerizable phthalocyanine-based colorant are exemplified, for example, by (meth)acrylolated tetraamino copper phthalocyanine and (meth)acrylolated (dodecanoylated tetraamino copper phthalocyanine).

Specified examples of the polymerizable UV-absorbing colorant capable of being used in combination for the purpose as described above are exemplified, for example, by benzophenone-based polymerizable UV-absorbing colorants including, for example, 2,4-dihydroxy-3-(p-styrenoazo)benzophenone, 2,4-dihydroxy-5-(p-styrenoazo)benzophenone, 2,4-dihydroxy-3-(p-(meth)acryloyloxymethylphenylazo) benzophenone, 2,4-dihydroxy-5-(p-(meth)acryloyloxymethylphenylazo)benzophenone, 2,4-dihydroxy-3-(p-(meth)acryloyloxyethylphenylazo)benzophenone, 2,4-dihydroxy-5-(p-(meth)acryloyloxyethylphenylazo)benzophenone, 2,4-dihydroxy-3-(p-(meth)acryloyloxypropylphenylazo) benzophenone, 2,4-dihydroxy-5-(p-(meth)acryloyloxypropylphenylazo)benzophenone, 2,4-dihydroxy-3-(o-(meth)acryloyloxymethylphenylazo)benzophenone, 2,4-dihydroxy-5-(o-(meth)acryloyloxymethylphenylazo) benzophenone, 2,4-dihydroxy-3-(o-(meth)acryloyloxyethylphenylazo)benzophenone, 2,4-dihydroxy-5-(o-(meth)acryloyloxyethylphenylazo)benzophenone, 2,4-dihydroxy-3-(o-(meth)acryloyloxypropylphenylazo)benzophenone, 2,4-dihydroxy-5-(o-(meth)acryloyloxypropylphenylazo) benzophenone, 2,4-dihydroxy-3-(p-(N,N-di(meth)acryloyloxyethylamino)phenylazo)benzophenone, 2,4-dihydroxy-5-(p-(N,N-di(meth)acryloyloxyethylamino)phenylazo) benzophenone, 2,4-dihydroxy-3-(o-(N,N-di(meth)acryloyloxyethylamino)phenylazo)benzophenone, 2,4-dihydroxy-5-(o-(N,N-di(meth)acryloylethylamino) phenylazo)benzophenone, 2,4-dihydroxy-3-(p-(N-ethyl-N-(meth)acryloyloxyethylamino)phenylazo)benzophenone, 2,4-dihydroxy-5-(p-(N-ethyl-N-(meth)acryloyloxyethylamino)phenylazo)benzophenone, 2,4-dihydroxy-3-(o-(N-ethyl-N-(meth)acryloyloxyethylamino)phenylazo)benzophenone, 2,4-dihydroxy-5-(o-(N-ethyl-N-(meth)acryloyloxyethylamino)phenylazo)benzophenone, 2,4-dihydroxy-3-(p-(N-ethyl-N-(meth)acryloylamino) phenylazo)benzophenone, 2,4-dihydroxy -5-(p-(N-ethyl-N-(meth)acryloylamino)phenylazo) benzophenone, 2,4-dihydroxy-3-(o-(N-ethyl-N-(meth)acryloylamino) phenylazo)benzophenone, and 2,4-dihydroxy-5-(o-(N-ethyl-N-(meth)acryloylamino)phenylazo)benzophenone; and benzoic acid-based polymerizable UV-absorbing colorants including, for example, 2-hydroxy-4-(p-styrenoazo) benzoic acid phenylester. These compounds can be used singly, or two or more species of these compounds can be used in mixture.

When the polymer of the present invention is copolymerized, it is possible to form a three-dimensional cross-linked structure in the polymer obtained by blending a cross-linking agent and/or using, as the copolymerizable monomer, a macromonomer having two or more polymerizable groups in the molecule. Accordingly, it is possible to improve the mechanical strength and the hardness of the polymer, and/or it is possible to suppress the elution of the monomer (including the colorant compound of the present invention) from the polymer. Further, when the polymer of the present invention is used as the material for the intraocular lens as described later on, then it is also possible to obtain the intraocular lens which is uniform and transparent, which has no distortion or no strain, and which is excellent in the optical characteristic, and/or it is also possible to apply the durability (resistance against chemicals, resistance against heat, and resistance against solvents) to the intraocular lens.

When the cross-linking agent and/or the macromonomer is/are blended, it is preferable that the cross-linking agent and/or the macromonomer is/are used at the blending ratio within a range of the ratio of 0.01 to 10 parts by weight per 100 parts by weight of the mixture of all of the copolymerizable monomers. If the ratio is less than 0.01 parts by weight, the effect is hardly obtained. On the other hand, if the ratio exceeds 10 parts by weight, there is a tendency that the obtained polymer becomes fragile.

The macromonomer as described above is exemplified, for example, by butanediol di(meth)acrylate, ethylene glycol di(meth)acrylate, diethylene glycol di(meth)acrylate, triethylene glycol di(meth)acrylate, propylene glycol di(meth)acrylate, dipropylene glycol di(meth)acrylate, diallyl fumarate, allyl (meth)acrylate, vinyl (meth)acrylate, trimethylolpropane tri(meth)acrylate, methacryloyloxyethyl (meth)acrylate, divinylbenzene, diallyl phthalate, diallyl adipate, triallyl diisocyanate, α-methylene-N-vinylpyrrolidone, 4-vinylbenzyl (meth)acrylate, 3-vinylbenzyl (meth)acrylate, 2,2-bis((meth)acryloyloxyphenyl)hexafluoropropane, 2,2-bis((meth)acryloyloxyphenyl)propane, 1,4-bis(2-(meth)acryloyloxyhexafluoroisopropyl)benzene, 1,3-bis(2-(meth)acryloyloxyhexafluoroisopropyl)benzene, 1,2-bis(2-(meth)acryloyloxyhexafluoroisopropyl)benzene, 1,4-bis(2-(meth)acryloyloxyisopropyl)benzene, 1,3-bis(2-(meth)acryloyloxyisopropyl)benzene, and 1,2-bis(2-(meth)acryloyloxyisopropyl)benzene.

Further, it is also possible to apply various functionalities to the polymer of the present invention by selecting appropriate copolymerizable monomer or monomers.

When the oxygen permeability is applied to the polymer of the present invention, it is appropriate to select, as the copolymerizable monomer, for example, silicon-containing monomers such as silicon-containing (meth)acrylates, silicon-containing styrene derivatives and the like, and fluorine-containing alkyl (meth)acrylates.

When the strength of the polymer is raised and/or the hardness is regulated, it is appropriate to select, as the copolymerizable monomer, for example, alkyl (meth)acrylates and styrene derivatives including styrene or (meth)acrylic acid.

When fluorine-containing monomers, which include, for example, fluorine-containing alkyl (meth)acrylates and fluorine-containing styrene derivatives, are selected as the copolymerizable monomer, it is possible to apply the function against the pollution with lipid when the polymer of the present invention is used as the material for the intraocular lens as described later on.

When the hydrophilicity is applied to the polymer of the present invention, it is appropriate to select, as the copolymerizable monomer, monomers having hydrophilic groups including, for example, hydroxy(meth)acrylates, (meth)acrylamides, aminoalkyl(meth)acrylates, (meth)acrylate, and N-vinyllactams. It is possible to obtain the hydrous and soft intraocular lens when the polymer of the present invention is used as the material for the intraocular lens as described later on.

When monomers containing aromatic rings including, for example, styrene-based monomers and aromatic ring-containing (meth)acrylates are selected as the copolymerizable monomer, the polymer of the present invention can be used as the material for the lens having a high refractive index.

When the copolymerizable monomer, which is usable to apply the various functionalities to the polymer of the present invention, is selected and blended as described above, the adjustment is appropriately made so that the copolymerizable monomer is preferably not less than 0.01 parts by weight and more preferably not less than 0.05 parts by weight with respect to 100 parts by weight of the mixture of all of the copolymerizable monomers, and the copolymerizable monomer is not more than 5 parts by weight and more preferably not more than 3 parts by weight with respect to 100 parts by weight of the mixture of all of the copolymerizable monomers.

As described above, the colorant compound of the present invention has the light beam absorption characteristic in the UV region (wavelength: not more than 380 nm) and the blue region (wavelength: 380 to 500 nm). Therefore, the polymer of the present invention can shut off the ultraviolet light, and the polymer of the present invention can reduce the intensity of the light in the blue region. Specifically, it is preferable that the light beam transmittance is decreased from a wavelength in the vicinity of 500 nm, and the light beam transmittance is 0% at wavelengths of not more than 400 nm. More preferably, when the UV-visible absorption spectrum is measured, then the rising in the chart sharply appears in the vicinity of 420 to 500 nm, and the colorant compound of the present invention is more excellent in the light beam transmittance suppressing ability in the UV/blue region than the conventional colorant compound (for example, BMAC). Further, in order not to allow the light having the wavelength of not more than 400 nm to be transmitted, it is preferable to use any other UV absorber. Therefore, when the colorant compound of the present invention is used as the material for the intraocular lens as described later on, it is possible to suppress the harmful influence of the light beam on the eye.

In the polymer of the present invention, the colorant compound of the present invention is directly bonded to the polymer chain by means of the copolymerization. Therefore, the colorant compound of the present invention is not eluted from the polymer of the present invention. This feature can be confirmed by the fact that no change occurs in the spectrum of the light beam transmittance between before and after the immersion of the polymer of the present invention for 24 hours in ethanol at 40° C.

Further, as described above, the amide bond, which connects the polymerizable group and the colorant moiety in the colorant compound of the present invention, is stable even under the alkaline conditions (for example, at pH of not less than 12). Therefore, the colorant moiety is not eliminated from the polymer of the present invention. As a result, the stability under the alkaline conditions, which has been deficient in any copolymer based on the use of the conventional colorant compound having the ester bond, is realized. The high light beam absorption characteristic can be also maintained in the polymer after the alkali treatment. This feature can be confirmed by the fact that the light beam transmittance, which is brought about by an immersion solution obtained after immersing the polymer of the present invention in a 4N sodium hydroxide aqueous solution at room temperature for 4 hours, is substantially 100%.

<3> Intraocular Lens of the Present Invention

The polymer of the present invention can be used as the material for the intraocular lens.

In general, when a colorant compound is added to the polymer, the colorant compound raises the hardness. On the contrary, the colorant compound of the present invention is excellent in the softness or flexibility. Therefore, the intraocular lens of the present invention, which is molded by using the polymer of the present invention as the material for the intraocular lens, can be expected to retain the softness, and the intraocular lens of the present invention is easily handled when the surgical operation is performed.

Further, the polymer of the present invention exhibits the excellent resistance against the light and the chemical agents, the polymer of the present invention has the high fastness property, and the colorant moiety is not eluted from the polymer as well. Therefore, it is possible to obtain the excellent intraocular lens which has the high safety and which suffers neither decolorization nor discoloration.

Other than the above, the polymer of the present invention can be also used as materials, for example, for glasses, sunglasses, contact lenses, and the polymer of the present invention can be also used for paints and building materials.

Further, the polymer of the present invention has the chemically stable colorant moiety, and the polymer of the present invention can be used without any deterioration even outdoors and in severe environments in which it is estimated that the temperature change and the pH change may be intense.

When the polymer of the present invention is used as the material for the intraocular lens, the molding can be performed in accordance with any known method. For example, the following technique is exemplified. That is, the polymerization reaction is performed in an appropriate mold or a vessel to obtain a rod-shaped, block-shaped, or plate-shaped polymer. After that, the polymer is processed to have a desired shape by means of the mechanical processing including, for example, the cutting processing and the polishing processing. Alternatively, the polymerization reaction is performed in a mold corresponding to a desired shape to obtain a polymer molded product, followed by mechanically applying the finishing processing, if necessary.

The support portion of the intraocular lens may be manufactured distinctly from the intraocular lens, and the support portion may be thereafter attached. Alternatively, no problem arises even when the support portion of the intraocular lens is molded simultaneously (integrally) with the intraocular lens.

When the polymer of the present invention is molded to provide the intraocular lens, it is also allowable that the surface modification treatment is applied, if necessary, in order to make the surface of the lens hydrophilic. It is preferable to perform the plasma treatment or the treatment based on the ultraviolet light. It is more preferable to perform the corona discharge treatment, the glow discharge treatment, or the UV/ozone treatment. When the treatment is performed as described above, any ordinary apparatus and any ordinary methods, which have been hitherto known, can be used as the treatment apparatus and the treatment method.

EXAMPLES

Synthesis of Polymerizable Aminoaryl Compound 1

An example, in which an aminoaryl compound was used as a starting material, is shown below, in relation to the exemplary synthesis of the polymerizable aminoaryl compound used for synthesizing the colorant compound of the present invention.

Synthesis Example 1

Synthesis of N-[2-[4-(tert-butoxycarbonylamino)phenyl]ethyl]methacrylamide

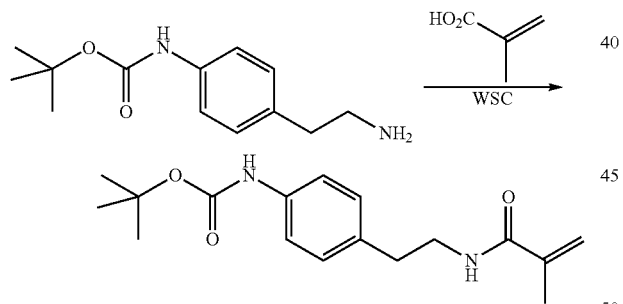

2-[4-(tert-Butoxycarbonyl)phenyl]ethylamine (3.54 g) and methacrylic acid (1.57 g) were dissolved in chloroform (80 mL), to which water-soluble carbodiimide (2.88 g) was added while being cooled with ice. The mixture was stirred at 4° C. for 1 hour, then at room temperature overnight, and concentrated under reduced pressure. The residue was washed with 5% potassium hydrogensulfate, saturated sodium hydrogencarbonate, and brine, dried with anhydrous magnesium sulfate, and concentrated under reduced pressure. The resulting residue was applied to silica gel column chromatography and eluted with hexane-ethyl acetate (volume ratio: 2:1) and subsequently with hexane-ethyl acetate (volume ratio: 1:1). The desired compound was obtained as white needles. The yield was 2.92 g. Spectrum data of $^1$H-NMR (400 MHz, CDCl$_3$) is shown for the obtained compound.

δ: 1.52 (s, 9H), 1.91 (s, 3H), 2.80 (t, 2H, J=6.8 Hz), 3.54 (q, 2H, J=6.8 Hz), 5.28 (t, 1H, J=1.4 Hz), 5.59 (s, 1H), 5.76 (br.s, 1H), 6.46 (br.s, 1H), 7.12 (d, 2H, J=8.3 Hz), 7.31 (d, 2H, J=8.3 Hz).

Synthesis Example 2

Synthesis of N-[2-[4-(tert-butoxycarbonylamino)phenyl]ethyl]acrylamide

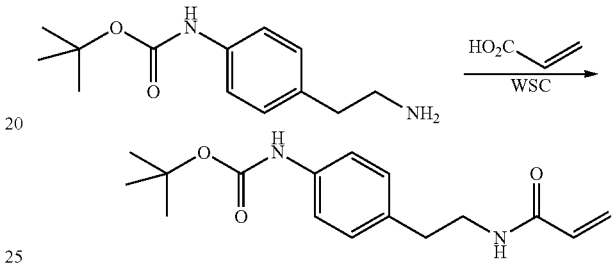

2-[4-(tert-Butoxycarbonyl)phenyl]ethylamine (2.36 g) and acrylic acid (0.84 g) were reacted in the same manner as in Synthesis Example 1, and the objective compound was obtained as white needles. The yield was 2.02 g. Spectrum data of $^1$H-NMR (400 MHz, CDCl$_3$) is shown for the obtained compound.

δ: 1.52 (s, 9H), 2.80 (t, 2H, J=6.8 Hz), 3.57 (q, 2H, J 6.8 Hz), 5.51 (br.s, 1H), 5.62 (dd, 1H, J=10.5 Hz, 0.9 Hz), 6.01 (dd, 1H, J=17.4 Hz, 10.5 Hz), 6.26 (dd, 1H, J=17.4 Hz, 0.9 Hz), 6.45 (br.s, 1H), 7.12 (d, 2H, J=8.2 Hz), 7.30 (d, 2H, J=8.2 Hz).

Synthesis Example 3

Synthesis of N-[4-(tert-butoxycarbonylamino)benzyl]methacrylamide

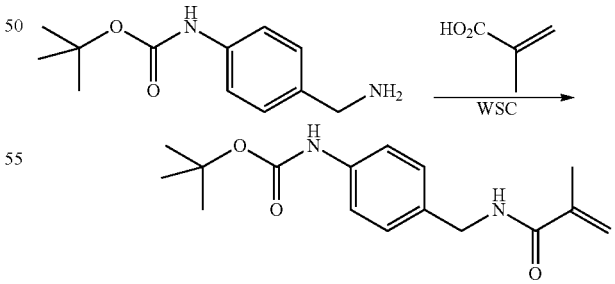

4-(tert-Butoxycarbonylamino)benzylamine (5.38 g) and methacrylic acid (1.89 g) were reacted in the same manner as in Synthesis Example 1, and the objective compound was obtained as white needles. The yield was 4.15 g. Spectrum data of $^1$H-NMR (400 MHz, CDCl$_3$) is shown for the obtained compound.

δ: 1.50 (s, 9H), 1.96 (s, 3H), 4.43 (d, 2H, J=5.4 HZ), 5.32 (t, 1H, J=0.3 Hz), 5.68 (s, 1H), 5.96 (br.s, 1H), 6.46 (br.s, 1H), 7.21 (d, 2H, J=8.8 Hz), 7.32 (d, 2H, J=8.8 Hz).

Synthesis of Polymerizable Aminoaryl Compound 2

An example, in which a nitroaryl compound was used as a starting material, is shown below, in relation to the exemplary synthesis of the polymerizable aminoaryl compound used for synthesizing the colorant compound of the present invention.

Synthesis Example 4

Synthesis of N-[2-(4-aminophenyl)ethyl]methacrylamide

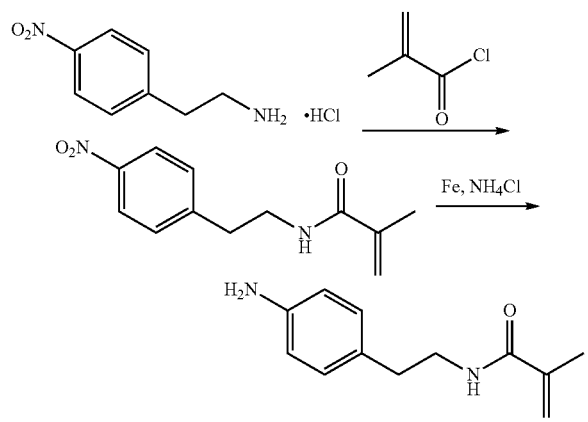

2-(4-Nitrophenyl)ethylamine hydrochloride (1.72 g) and sodium hydrogencarbonate (5.00 g) were dissolved in water (25 mL), to which ethyl acetate (25 mL) was added, followed by being stirred in an ice bath. Methacryloyl chloride (1.79 g) was added dropwise thereto. After stirring for 10 minutes, the organic layer was separated. The aqueous layer was extracted with ethyl acetate, the organic layers were combined, washed with water and brine, dried over anhydrous sodium sulfate, and evaporated under reduced pressure. The recrystallization was performed by using a mixture solvent of hexane and ethyl acetate. N-[2-(4-Nitrophenyl)ethyl]methacrylamide was obtained as pale yellowish crystals. The yield was 1.25 g (63%). Spectrum data of $^1$H-NMR (400 MHz, CDCl$_3$) is shown for the obtained compound.

δ: 1.93 (s, 3H), 2.99 (t, 2H, J=6.8 Hz), 3.60 (q, 2H, J 6.8 Hz), 5.32 (t, 1H, J=1.2 Hz), 5.61 (s, 1H), 5.82 (br.s, 1H), 7.37 (d, 2H, J=8.6 Hz), 8.17 (d, 2H, J=8.6 Hz).

Subsequently, N-[2-(4-nitrophenyl)ethyl]methacrylamide (1.20 g) was dissolved in ethanol (15 mL) and water (5 mL). Ammonium chloride (364 mg) and iron powder (933 mg) were added, and the reflux was performed at 80° C. for 4 hours. Iron powder was collected by the filtration, and the filtrate was evaporated under the reduced pressure. Water and ethyl acetate were added to the residual oil and the organic layer was separated. The organic layer was washed with water and brine, dried over anhydrous sodium filfate, and evaporated to give the desired compound as a pale red oily substance. The yield was 1.01 g (97%). Spectrum data of $^1$H-NMR (400 MHz, CDCl$_3$) is shown for the obtained compound.

δ: 1.91 (s, 3H), 2.74 (t, 2H, J=6.8 Hz), 3.51 (q, 2H, J 6.8 Hz), 3.61 (br.s, 2H), 5.27 (t, 1H, J=1.4 Hz), 5.59 (s, 1H), 5.76 (br.s, 1H), 6.64 (d, 2H, J=8.3 Hz), 6.98 (d, 2H, J=8.3 Hz).

Synthesis Example 5

Synthesis of N-(4-aminobenzyl)methacrylamide

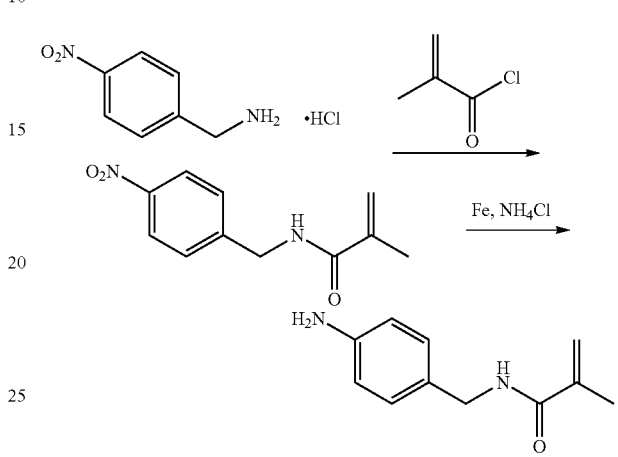

4-Nitrobenzylamine hydrochloride (1.51 g) and sodium hydrogencarbonate (4.13 g) were dissolved in water (25 mL), to which ethyl acetate (25 mL) was added, followed by being stirred in an ice bath. Methacryloyl chloride (1.26 g) was added dropwise thereto. After stirring for 10 minutes, the mixture was extracted with ethyl acetate. After washing with water and brine, the organic layer was dried over anhydrous sodium sulfate and evaporated. After that, the recrystallization was performed by using a mixture solvent of hexane and ethyl acetate. N-(4-Nitrobenzyl)methacrylamide was obtained as pale yellowish crystals. The yield was 1.05 g (60%). Spectrum data of $^1$H-NMR (400 MHz, CDCl$_3$) is shown for the obtained compound.

δ: 2.01 (s, 3H), 4.61 (d, 2H, J=6.0 Hz), 5.41 (t, 1H, J=1.0 Hz), 5.76 (t, 1H, J=1.0 Hz), 6.29 (br.s, 1H), 7.45 (d, 2H, J=8.8 Hz), 8.17 (d, 2H, J=8.8 Hz).

Subsequently, N-(4-nitrobenzyl)methacrylamide (811 mg) was dissolved in ethanol (12 mL) and water (4 mL). Ammonium chloride (183 mg) and iron powder (573 mg) were added, and the reflux was performed at 80° C. for 4 hours. Iron powder was collected by the filtration, and the filtrate was evaporated. Water and ethyl acetate were added to the residue and the organic layer was separated. The organic layer was dried over anhydrous sodium sulfate and evaporated to give a pale red oily substance. The yield was 580 mg (89%). Spectrum data of $^1$H-NMR (400 MHz, CDCl$_3$) is shown for the obtained compound.

δ: 1.97 (t, 3H, J=1.3 Hz), 3.67 (br.s, 2H), 4.37 (d, 2H, J=5.6 Hz), 5.31 (t, 1H, J=1.4 Hz), 5.68 (br.t, 1H), 5.92 (br. s, 1H), 6.65 (d, 2H, J=8.3 Hz), 7.09 (d, 2H, J=8.3 Hz).

Synthesis of Polymerizable UV-Absorbing Colorant

The polymerizable UV-absorbing colorant of the present invention was synthesized by using the polymerizable aminoaryl compound synthesized as described above. Examples 1 to 12 are shown below in relation thereto.

Example 1

Synthesis of 2,4-dihydroxy-5-[4-[2-(methacrylamide)ethyl]phenylazo]benzophenone (hereinafter referred to with an abbreviation of "HBZ-PHM")

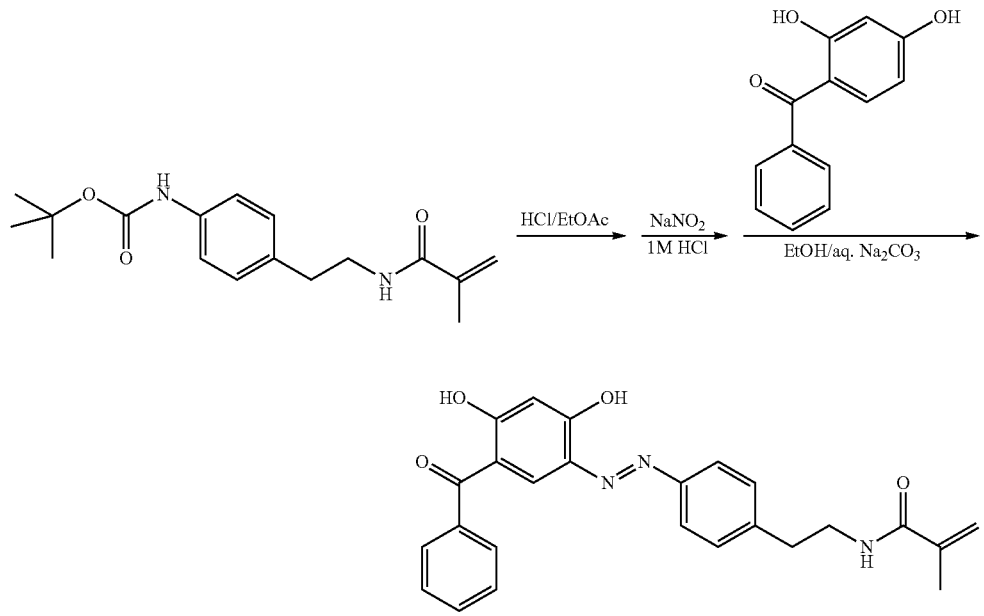

N-[2-[4-(tert-Butoxycarbonylamino)phenyl]ethyl]methacrylamide (609 mg) was dissolved in ethyl acetate (2 mL), to which 4 M hydrogen chloride in ethyl acetate (5 mL) was added. The mixture was stirred for 40 minutes at room temperature, followed by being concentrated under reduced pressure. The residue was dissolved in 1 M hydrochloric acid (4 mL), to which an aqueous solution (10 mL) of sodium nitrite (145 mg) was added dropwise while being cooled with ice, followed by being stirred at 4° C. for 40 minutes to prepare a diazonium salt. Subsequently, 2,4-dihydroxybenzophenone (428 mg) was dissolved in ethanol (20 mL), to which an aqueous solution (20 mL) of sodium carbonate (423 mg) was added. A solution containing the diazonium salt described above was added dropwise to the mixture while being cooled with ice. The mixture was stirred at 4° C. for 1 hour, and then at room temperature for 4 hours, while 4 M hydrochloric acid was added dropwise to adjust pH to 6. Water (40 mL) was added to the mixture, and the precipitate was collected by the filtration, followed by being washed with water. The precipitate was dissolved in chloroform without being dried, which was dried over anhydrous magnesium sulfate and evaporated. Methanol was added to the residue and allowed to stand at 4° C. overnight. After that, the precipitated objective compound was obtained as orange crystals. The yield was 326 mg (38%). Spectrum data of $^1$H-NMR (400 MHz, CDCl$_3$) is shown for the obtained compound.

$^1$H-NMR (400 MHz, CDCl$_3$) δ: 1.93 (t, 3, J=1.0 Hz), 2.94 (t, 2H, J=6.8 Hz), 3.61 (q, 2H, J=6.8 Hz), 5.31 (t, 1H, J=1.0 Hz), 5.61 (t, 1H, J=1.0 Hz), 5.80 (br.t, 1H), 6.58 (s, 1H), 7.33 (d, 2H, J=8.8 Hz), 7.56 (t, 2H, J=7.2 Hz), 7.64 (tt, 1H, J=7.3 Hz, 2.4 Hz), 7.73-7.76 (m, 4H), 8.23 (s, 1H), 12.89 (s, 1H), 13.94 (s, 1H).

Example 2

Synthesis of 2-hydroxy-5-[4-[2-(methacrylamide)ethyl]phenylazo]benzophenone (hereinafter referred to with an abbreviation of "NBZ-PHM")

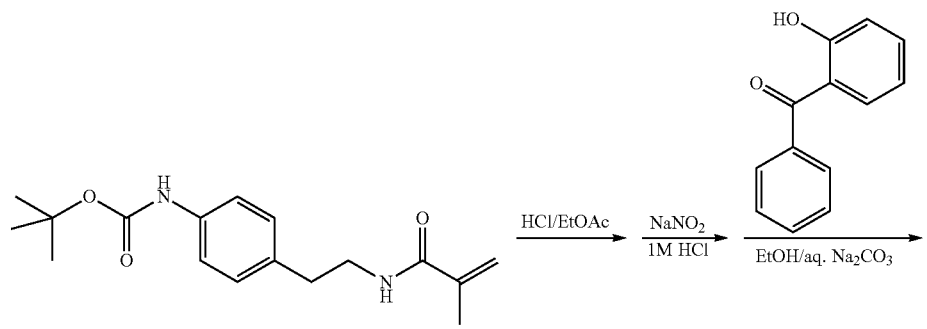

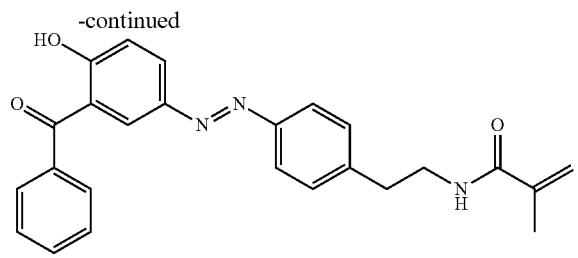

In the same manner as in Example 1, N-[2-[4-(tert-butoxycarbonylamino)phenyl]ethyl]methacrylamide (609 mg) was subjected to the acid treatment, followed by being converted into a diazonium salt to perform the diazo coupling with 2-hydroxybenzophenone (396 mg). The objective compound was obtained as orange crystals. The yield was 630 mg (76%). Spectrum data of $^1$H-NMR (400 MHz, CDCl$_3$) is shown for the obtained compound.

$^1$H-NMR (400 MHz, CDCl$_3$) δ: 1.92 (s, 3H), 2.93 (t, 2H, J 6.8 Hz), 3.61 (q, 2H, J=6.8 Hz), 5.29 (t, 1H, J=1.2 Hz), 5.61 (s, 1H), 5.79 (br.t, 1H), 7.20 (d, 1H, J=8.8 Hz), 7.32 (d, 2H, J=8.3 Hz), 7.57 (t, 2H, J=7.3 Hz), 7.66 (t, 1H, J=7.3 Hz), 7.77-7.81 (m, 4H), 8.15 (dd, 1H, J=9.3 Hz, 2.4 Hz), 8.26 (d, 1H, J=2.4 Hz), 12.44 (s, 1H).

Example 3

Synthesis of 2-hydroxy-5-[4-[2-(methacrylamide) ethyl]phenylazo]-4-methoxybenzophenone (hereinafter referred to with an abbreviation of "MBZ-PHM")

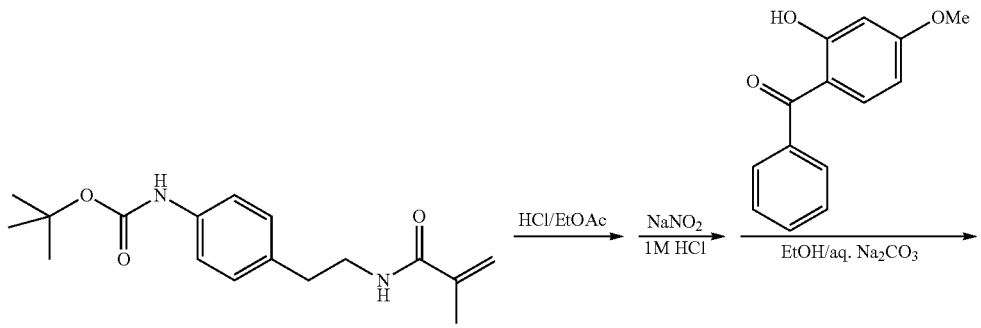

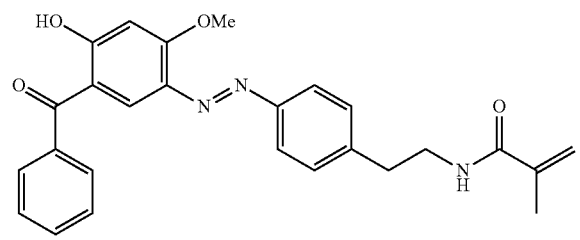

In the same manner as in Example 1, N-[2-[4-(tert-butoxycarbonylamino)phenyl]ethyl]methacrylamide (609 mg) was subjected to the acid treatment, followed by being converted into a diazonium salt to perform the diazo coupling with 2-hydroxy-4-methtoxybenzophenone (456 mg). The objective compound was obtained as orange crystals. The yield was 553 mg (62%). Spectrum data of $^1$H-NMR (400 MHz, CDCl$_3$) is shown for the obtained compound.

$^1$H-NMR (400 MHz, CDCl$_3$) δ: 1.92 (s, 3H), 2.92 (t, 2H, J 6.8 Hz), 3.60 (q, 2H, J=6.8 Hz), 4.09 (s, 3H), 5.29 (t, 1H, J=1.4 Hz), 5.60 (s, 1H), 5.76 (br.t, 1H), 6.71 (s, 1H), 7.29 (d, 2H, J=8.8 Hz), 7.53 (t, 2H, J=8.8 Hz), 7.61 (t, 1H, J=7.8 Hz), 7.71 (d, 2H, J=6.8 Hz), 7.76 (d, 2H, J=6.8 Hz), 8.03 (s, 1H), 12.91 (s, 1H).

Example 4

Synthesis of 4-ethoxy-2-hydroxy-5-[4-[2-(methacrylamide)ethyl]phenylazo]benzophenone (hereinafter referred to with an abbreviation of "EBZ-PHM")

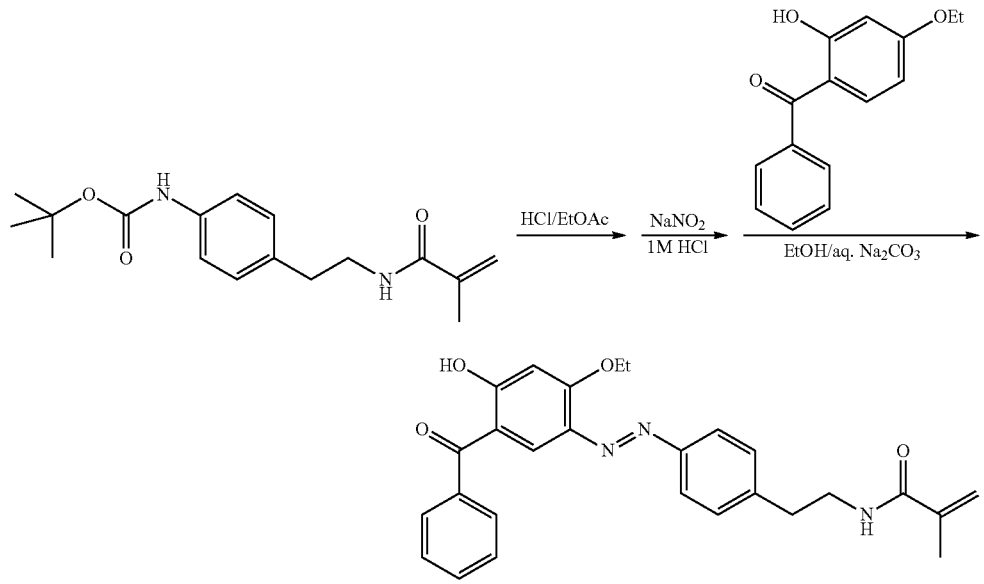

In the same manner as in Example 1, N-[2-[4-(tert-butoxycarbonylamino)phenyl]ethyl]methacrylamide (609 mg) was subjected to the acid treatment, followed by being converted into a diazonium salt to perform the diazo coupling with 4-ethoxy-2-hydroxybenzophenone (485 mg). The objective compound was obtained as orange crystals. The yield was 652 mg (71%). Spectrum data of $^1$H-NMR (400 MHz, CDCl$_3$) is shown for the obtained compound.

$^1$H-NMR (400 MHz, CDCl$_3$) δ: 1.59 (t, 3H, J=6.8 Hz), 1.92 (s, 3H), 2.92 (t, 2H, J=6.8 Hz), 3.60 (q, 2H, J=6.8 Hz), 4.33 (q, 2H, J=6.8 Hz), 5.29 (t, 1H, J=1.2 Hz), 5.60 (s, 1H), 5.77 (br.t, 1H), 6.68 (s, 1H), 7.30 (d, 2H, J=8.3 Hz), 7.53 (t, 2H, J=7.3 Hz), 7.61 (t, 1H, J=7.3 Hz), 7.71 (d, 2H, J=7.3 Hz), 7.78 (d, 2H, J=8.4 Hz), 8.03 (s, 1H), 12.90 (s, 1H).

Example 5

Synthesis of 5-[4-[2-(acrylamide)ethyl]phenylazo]-2,4-dihydroxybenzophenone (hereinafter referred to with an abbreviation of "HBZ-PHA")

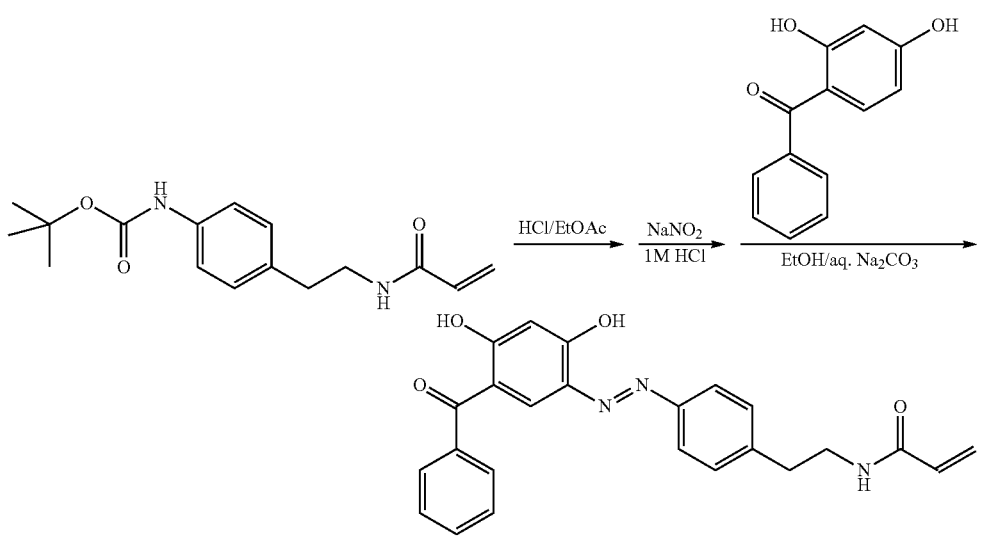

In the same manner as in Example 1, N-[2-[4-(tert-butoxycarbonylamino)phenyl]ethyl]acrylamide (581 mg) was subjected to the acid treatment, followed by being converted into a diazonium salt to perform the diazo coupling with 2,4-dihydroxybenzophenone (428 mg). The objective compound was obtained. The yield was 313 mg (38%). Spectrum data of $^1$H-NMR (400 MHz, CDCl$_3$) is shown for the obtained compound.

δ: 2.94 (t, 2H, J=6.8 Hz), 3.64 (q, 2H, J=6.4 Hz), 5.56 (br.t, 1H), 5.64 (dd, 1H, J=10.8 Hz, 1.5 Hz), 6.03 (dd, 1H, J=17.1 Hz, 10.8 Hz), 6.28 (dd, 1H, J=17.1 Hz, 1.5 Hz), 6.58 (s, 1H), 7.33 (d, 2H, J=8.3 Hz), 7.54-7.59 (m, 2H), 7.65 (t, 1H, J=78 Hz), 7.73-7.76 (m, 4H), 8.23 (s, 1H), 12.90 (s, 1H), 13.94 (s, 1H).

Example 6

Synthesis of 5-[4-[2-(acrylamide)ethyl]phenylazo]-2-hydroxy-4-methoxybenzophenone (hereinafter referred to with an abbreviation of "MBZ-PHA")

a diazonium salt to perform the diazo coupling with 2-hydroxy-4-methoxybenzophenone (456 mg). The objective compound was obtained. The yield was 510 mg (59%). Spectrum data of $^1$H-NMR (400 MHz, CDCl$_3$) is shown for the obtained compound.

δ: 2.92 (t, 2H, J=6.8 Hz), 3.62 (q, 2H, J=6.8 Hz), 4.09 (s, 3H), 5.56 (br.t, 1H), 5.63 (dd, 1H, J=10.2 Hz, 1.5 Hz), 6.02 (dd, 1H, J=17.1 Hz, 10.2 Hz), 6.26 (dd, 1H, J=17.1 Hz, 1.5 Hz), 6.70 (s, 1H), 7.29 (d, 2H, J=8.3 Hz), 7.53 (t, 2H, J=7.3 Hz), 7.61 (t, 1H, J=7.8 Hz), 7.70-7.76 (m, 4H), 8.03 (s, 1H), 12.92 (s, 1H).

Example 7

Synthesis of 5-[4-[2-(acrylamide)ethyl]phenylazo]-4-ethoxy-2-hydroxybenzophenone (hereinafter referred to with an abbreviation of "EBZ-PHA")

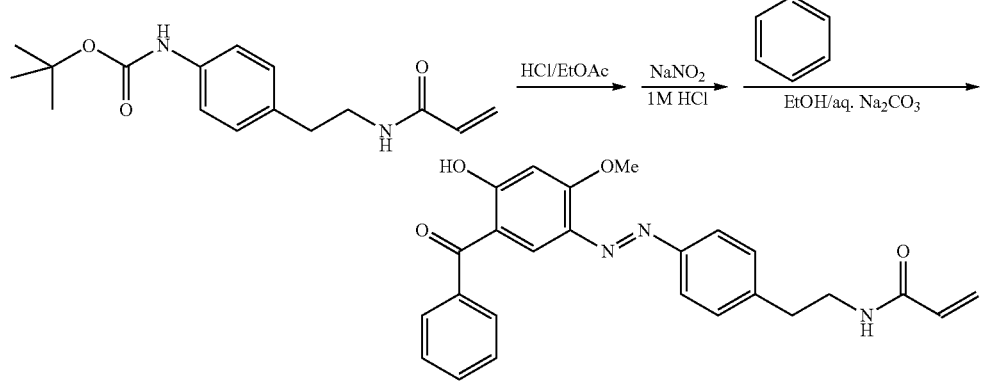

In the same manner as in Example 5, N-[2-[4-(tert-butoxycarbonylamino)phenyl]ethyl]acrylamide (581 mg) was subjected to the acid treatment, followed by being converted into

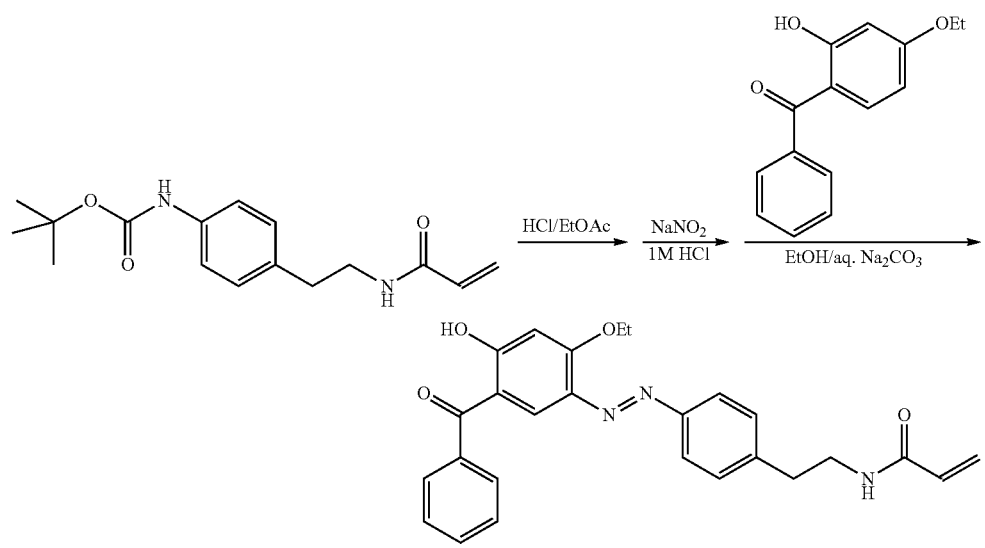

In the same manner as in Example 5, N-[2-[4-(tert-butoxy-carbonylamino)phenyl]ethyl]acrylamide (581 mg) was subjected to the acid treatment, followed by being converted into a diazonium salt to perform the diazo coupling with 4-ethoxy-2-hydroxybenzophenone (485 mg). The objective compound was obtained. The yield was 583 mg (66%). Spectrum data of $^1$H-NMR (400 MHz, CDCl$_3$) is shown for the obtained compound.

δ: 1.59 (t, 3H, J=7.1 Hz), 2.93 (t, 2H, J=6.9 Hz), 3.64 (q, 2H, J=6.9 Hz), 4.33 (q, 2H, J=7.1 Hz), 5.52 (br.t, 1H), 5.63 (dd, 1H, J=10.4 Hz, 1.3 Hz), 6.02 (dd, 1H, J=16.9 Hz, 10.4 Hz), 6.27 (dd, 1H, J=16.9 Hz, 1.3 Hz), 6.68 (s, 1H), 7.29 (d, 2H, J=8.5 Hz), 7.50-7.55 (m, 2H), 7.61 (t, 1H, J=7.4 Hz), 7.69-7.72 (m, 2H), 7.96 (d, 2H, J 8.3 Hz), 8.02 (s, 1H), 12.89 (s, 1H).

Example 8

Synthesis of 5-[4-[2-(acrylamide)ethyl]phenylazo]-2-hydroxybenzophenone (hereinafter referred to with an abbreviation of "NBZ-PHA")

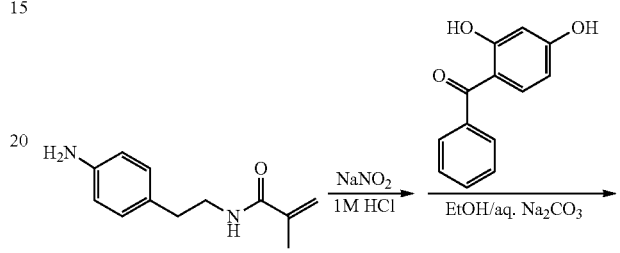

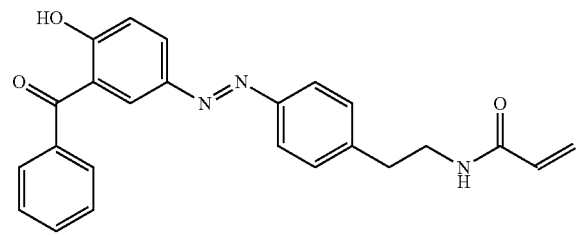

In the same manner as in Example 5, N-[2-[4-(tert-butoxy-carbonylamino)phenyl]ethyl]acrylamide (581 mg) was subjected to the acid treatment, followed by being converted into a diazonium salt to perform the diazo coupling with 2-hydroxybenzophenone (396 mg). The objective compound was obtained. The yield was 525 mg (66%). Spectrum data of $^1$H-NMR (400 MHz, CDCl$_3$) is shown for the obtained compound.

δ: 2.94 (t, 2H, J=6.8 Hz), 3.64 (q, 2H, J=6.8 Hz), 5.56 (br.t, 1H), 5.63 (dd, 1H, J=10.3 Hz, 1.5 Hz), 6.02 (dd, 1H, J=17.1 Hz, 10.3 Hz), 6.27 (dd, 1H, J=17.1 Hz, 1.5 Hz), 7.20 (d, 1H, J=9.3 Hz), 7.32 (d, 2H, J=8.3 Hz), 7.57 (tt, 2H, J=7.3 Hz, 1.5 Hz), 7.66 (t, 1H, J=7.8 Hz), 7.77-7.81 (m, 4H), 8.15 (dd, 1H, J=9.3 Hz, 2.4 Hz), 8.26 (d, 1H, J=2.4 Hz), 12.45 (s, 1H).

Example 9

Synthesis of 2,4-dihydroxy-5-[4-[2-(methacrylamide)ethyl]phenylazo]benzophenone (HBZ-PHM)

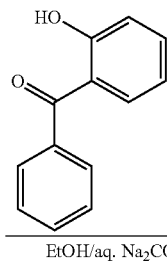

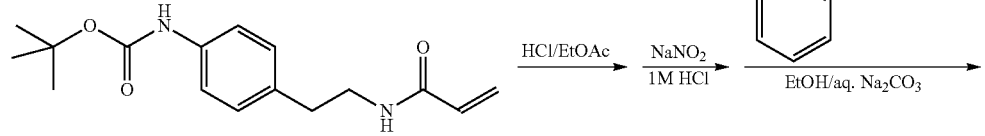

-continued

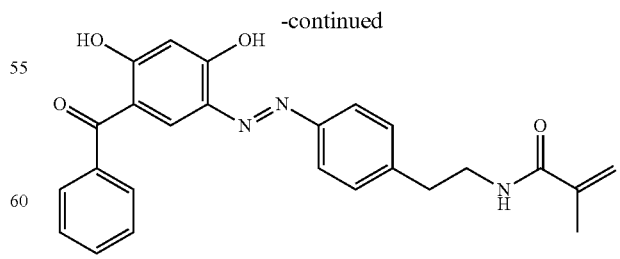

HBZ-PHM was synthesized in accordance with the following method different from the method of Example 1.

1 M hydrochloric acid (15 mL) was added to N-[2-[4-aminophenyl]ethyl]methacrylamide (930 mg), to which an aqueous solution (5 mL) of sodium nitrite (355 mg) was added dropwise while being cooled with ice, followed by being stirred at 4° C. for 1 hour to prepare a diazonium salt. Subsequently, 2,4-dihydroxybenzophenone (975 mg) was dissolved in ethanol (40 mL), to which an aqueous solution (40 mL) of sodium carbonate (970 mg) was added. The solution containing the diazonium salt described above was added dropwise to the mixture while being cooled with ice. The mixture was stirred at 4° C. for 1 hour, and then at room temperature for 2 hours, to which 4 M hydrochloric acid was added dropwise to adjust pH to 6. Water (40 mL) was added to the mixture, and the precipitate was collected by the filtration, followed by being washed with water. The precipitate was dissolved in chloroform after being dried, which was adsorbed to silica gel. The column chromatography was performed using ethyl acetate, and orange crystals were obtained. Methanol was added to the crystals to perform the reflux, followed by being left to stand at room temperature overnight. The precipitated objective compound was obtained as orange crystals. The yield was 774 mg (40%). Spectrum data of $^1$H-NMR (400 MHz, CDCl$_3$) is shown for the obtained compound.

δ: 1.93 (t, 3H, J=1.0 Hz), 2.94 (t, 2H, J=6.8 Hz), 3.61 (q, 2H, J=6.8 Hz), 5.31 (t, 1H, J=1.0 Hz), 5.61 (t, 1H, J=1.0 Hz), 5.81 (br.t, 1H), 6.58 (s, 1H), 7.33 (d, 2H, J=8.5 Hz), 7.56 (t, 2H, J=7.2 Hz), 7.64 (tt, 1H, J=7.2 Hz, 2.4 Hz), 7.72-7.76 (m, 4H), 8.22 (s, 1H), 12.89 (s, 1H), 13.93 (s, 1H).

Example 10

Synthesis of 5-[4-[2-(methacrylamide)methyl]phenylazo]-2,4-dihydroxybenzophenone (hereinafter referred to with an abbreviation of "HBZ-BZM")

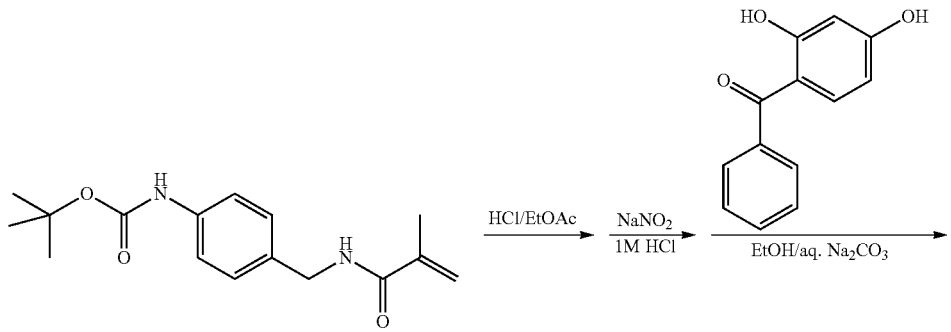

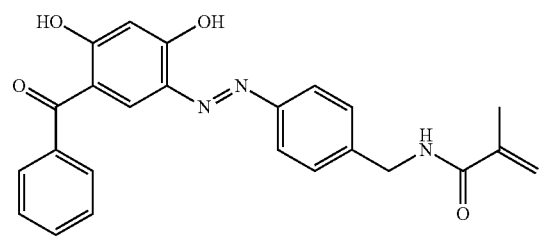

In the same manner as in Example 1, N-[4-(tert-butoxycarbonylamino)benzyl]methacrylamide (581 mg) was subjected to the acid treatment, followed by being converted into a diazonium salt to perform the diazo coupling with 2,4-dihydroxybenzophenone (428 mg). The objective compound was obtained. The yield was 470 mg (57%). Spectrum data of $^1$H-NMR (400 MHz, CDCl$_3$) is shown for the obtained compound.

δ: 1.99 (s, 3H), 4.56 (d, 2H, J=5.9 Hz), 5.37 (s, 1H), 5.73 (s, 1H), 6.13 (br.t, 1H), 6.57 (s, 1H), 7.25 (s, 1H), 7.41 (d, 2H, J=8.8 Hz), 7.53-7.57 (m, 2H), 7.63 (t, 1H, J=7.3 Hz), 7.72-7.76 (m, 4H), 8.22 (s, 1H), 12.88 (s, 1H), 13.89 (s, 1H).

Example 11

Synthesis of 5-[4-[2-(methacrylamide)methyl]phenylazo]-2-hydroxy-4-methoxybenzophenone (hereinafter referred to with an abbreviation of "MBZ-BZM")

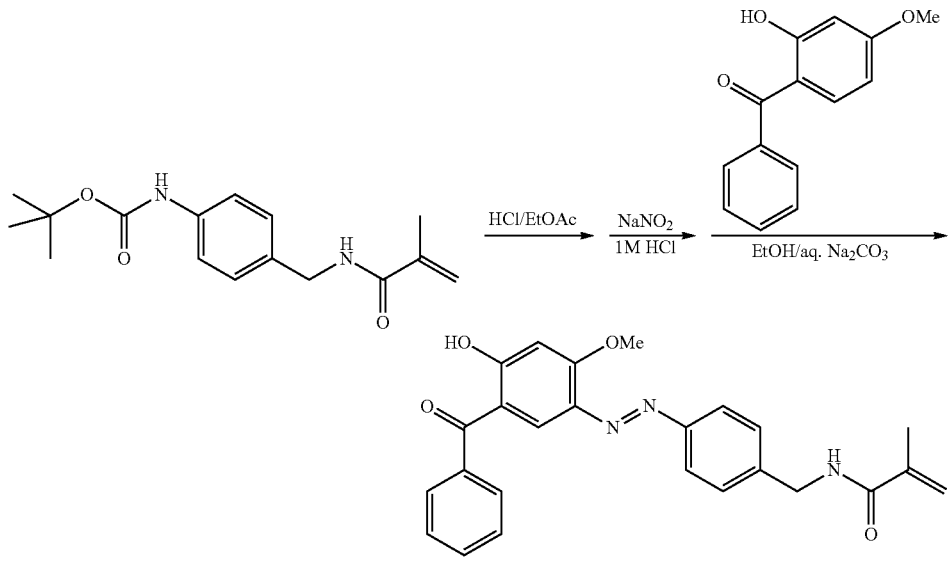

In the same manner as in Example 10, N-[4-(tert-butoxycarbonylamino)benzyl]methacrylamide (581 mg) was subjected to the acid treatment, followed by being converted into a diazonium salt to perform the diazo coupling with 2-hydroxy-4-methoxybenzophenone (456 mg). The objective compound was obtained. The yield was 511 mg (59%). Spectrum data of $^1$H-NMR (400 MHz, CDCl$_3$) is shown for the obtained compound.

δ: 2.00 (s, 3H), 4.09 (s, 3H), 4.56 (d, 2H, J=5.9 Hz), 5.37 (s, 1H), 5.73 (s, 1H), 6.10 (br.t, 1H), 6.70 (s, 1H), 7.39 (d, 2H, J=8.8 Hz), 7.51-7.55 (m, 2H), 7.61 (t, 1H, J=7.8 Hz), 7.69-7.72 (m, 2H), 7.78 (d, 2H, J=8.3 Hz), 8.03 (s, 1H), 12.92 (s, 1H).

Example 12

Synthesis of 5-[4-[2-(methacrylamide)methyl]phenylazo]-2-hydroxy-4-methoxybenzophenone (MBZ-BZM)

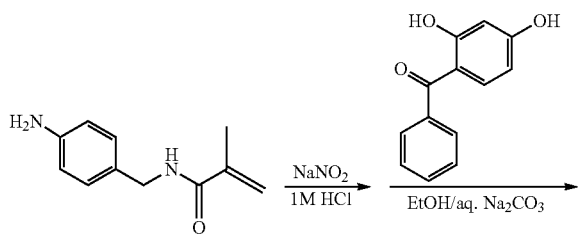

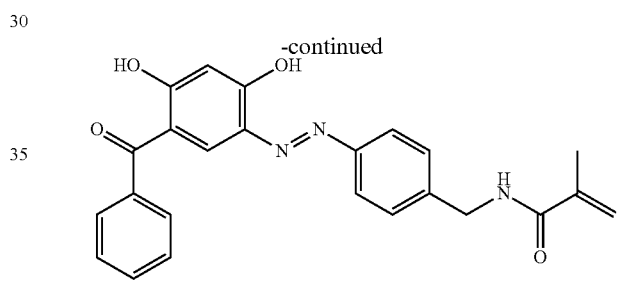

MBZ-BZM was synthesized in accordance with the following method different from the method of Example 11.

1 M hydrochloric acid (9 mL) was added to N-[4-aminobenzyl]methacrylamide (574 mg), to which an aqueous solution (3 mL) of sodium nitrite (210 mg) was added dropwise while being cooled with ice, followed by being stirred at 4° C. for 1 hour to prepare a diazonium salt. Subsequently, 2,4-dihydroxybenzophenone (637 mg) was dissolved in ethanol (25 mL), to which an aqueous solution (25 mL) of sodium carbonate (644 mg) was added. The solution containing the diazonium salt described above was added dropwise to the mixture while being cooled with ice. The mixture was stirred at 4° C. for 1 hour, and then at room temperature for 2 hours, to which 4 M hydrochloric acid was added dropwise to adjust pH to 6. Water (25 mL) was added to the mixture, and the precipitate was collected by the filtration, followed by being washed with water. The precipitate was dissolved in chloroform after being dried, which was adsorbed to silica gel. The column chromatography was performed with ethyl acetate, and orange crystals were obtained. Methanol was added to the crystals to perform the reflux, followed by being left to stand at room temperature overnight. The precipitated objective compound was obtained as orange crystals. The yield was 370 mg (29%). Spectrum data of $^1$H-NMR (400 MHz, CDCl$_3$) is shown for the obtained compound.

δ: 2.00 (t, 3H, J=1.1 Hz), 4.57 (d, 2H, J=6.0 Hz), 5.38 (t, 1H, J=1.4 Hz), 5.73 (br.t, 1H), 6.16 (br.s, 1H), 6.57 (s, 1H), 7.41 (d, 2H, J=8.5 Hz), 7.56 (t, 2H, J=7.4 Hz), 7.63 (tt, 1H, J=7.3 Hz, 2.4 Hz), 7.71-7.78 (m, 4H), 8.22 (s, 1H), 12.88 (s, 1H), 13.89 (s, 1H).

Exemplary Copolymerization of Polymerizable UV-Absorbing Colorant and Other Polymerizable Monomer The polymerizable UV-absorbing colorant obtained in Example was copolymerized with other polymerizable monomer.

Example 13

0.03 parts by mass of the polymerizable UV-absorbing colorant (HBZ-PHM) obtained in Example 1, 60 parts by mass of 2-phenoxyethyl acrylate, 40 parts by mass of ethyl acrylate, and 0.5 parts by mass of 2,2'-azobis(2,4-dimethylvaleronitrile) were blended uniformly or homogeneously, followed by being polymerized at 80° C. for 40 minutes to manufacture a polymer sheet having a thickness of 1 mm. The obtained polymer sheet was used as a sample to measure the light beam transmittance at wavelengths of 220 to 800 nm. A result is shown in FIG. 1.

Further, this sample was immersed in ethanol at 40° C. for 24 hours to perform the elution treatment, and then the light beam transmittance was measured again. As a result, the spectrum was not changed between before and after the elution treatment. This fact indicates that the polymerizable UV-absorbing colorant is chemically bonded in the material. It has been successfully confirmed that no elution is caused after the polymerization even when the colorant compound of the present invention is used for the polymer synthesis by using the same together with other UV absorber in combination. A UV-visible spectrophotometer was used to measure the light beam transmittance (the same was also used in the following procedures).

Exemplary Copolymerization of Polymerizable UV-Absorbing Colorant, Polymerizable UV Absorber, and Other Polymerizable Monomer The polymerizable UV-absorbing colorant obtained in Example was copolymerized with other polymerizable monomer together with other polymerizable UV absorber.

Example 14

Figure 2:
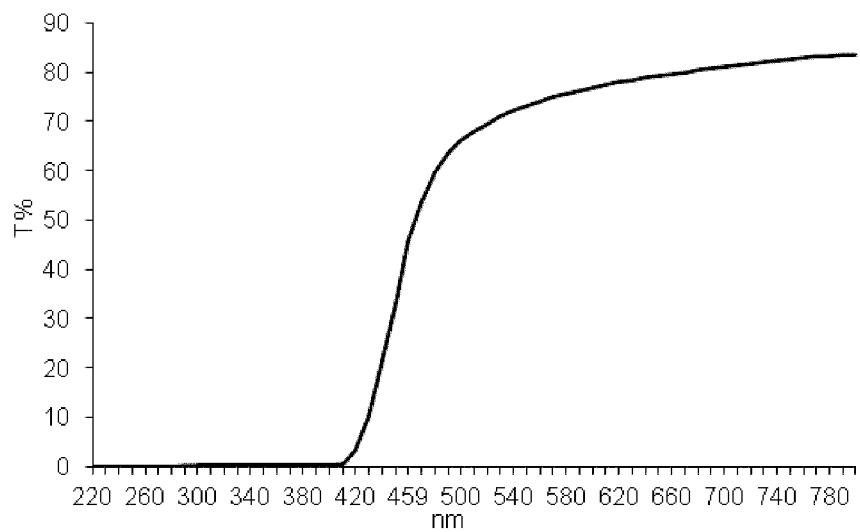
FIG. 2 shows a chart illustrating a UV-visible absorption spectrum of a polymer sheet obtained in Example 14.

A polymer sheet was prepared in the same manner as in Example 13 except that 0.15 parts by mass of 2-[2'-hydroxy-5'-(2"-methacryloyloxyethoxy)-3'-t-butylphenyl]-5-methyl-2H-benzotriazole was further blended as a UV absorber. The light beam transmittance was measured at wavelengths of 220 to 800 nm in the same manner as in Example 13 by using the obtained sheet as a sample. A result is shown in FIG. 2. The spectrum of the light beam transmittance was not changed between before and after the elution treatment. It has been successfully confirmed that the polymerizable UV-absorbing colorant of the present invention is incorporated as the copolymer component into the polymer, and the polymerizable UV-absorbing colorant of the present invention is not eluted after the polymerization, even when the polymerizable UV-absorbing colorant of the present invention is used together with other polymerizable UV absorber in combination.

Comparison of Stability Under Alkaline Condition

HBZ-PHM (1 part by weight) obtained in Example 1 and methyl methacrylate (26 parts by weight) were changed in a mixed solvent of dioxane (52 parts by weight), N,N-dimethylformamide (22 parts by weight), and water (20 parts by weight), to which 2.4 parts by weight of 2,2'-azobis(2,4-dimethylvaleronitrile) was added, followed by being polymerized at 75° C. for 5 hours under an argon atmosphere to obtain an HBZ-PHM copolymer.

As Comparison Example, 2,4-dihydroxy-5-(4-(2-(N-2-methacryloyloxyethyl)carbamoyloxy)ethylphenylazo) benzophenone (BMAC), which was synthesized in accordance with a procedure disclosed in Synthesis Example 1 of Patent Document 6 (JP2006-291006A), was used in place of HBZ-PHM to perform a polymerization reaction in the same manner as described above, and a BMAC copolymer was obtained.

Figure 3:
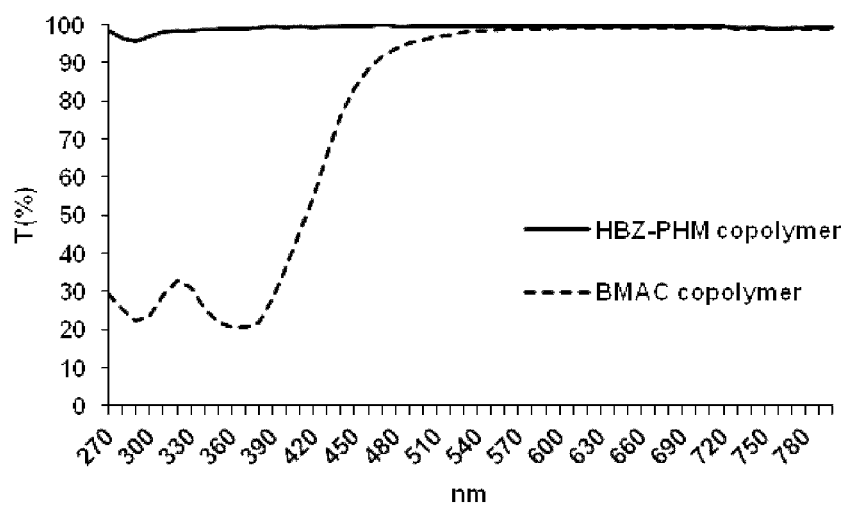
FIG. 3 shows a chart illustrating UV-visible absorption spectrums of filtrates obtained after alkali-treating polymers.

Powders of the polymers (200 mg), which were obtained after performing the Soxhlet extraction for 12 hours with ethanol for powders of the respective obtained copolymers, were suspended in ethanol (5 mL) respectively, to each of which 4 N NaOH (5 mL) was added, followed by being stirred at room temperature for 4 hours. The test solution in this situation exhibited that pH was 12 to 14 with pH test paper. After the completion of the stirring, the solution was neutralized with 4 N HCl, to which ethanol was further added. Insoluble matters were removed by the filtration, and the filtrate was observed. As a result, the filtrate was colorless and transparent in the case of the HBZ-PHM copolymer. On the other hand, the filtrate was colored to be yellow in the case of the BMAC copolymer. Further, FIG. 3 shows results of the measurement of the light beam transmittances at wavelengths of 220 to 800 nm for the respective filtrates. The filtrate of the BMAC copolymer after the alkali treatment exhibited the transmittance pattern which was the same as or equivalent to that of the BMAC copolymer. This fact strongly suggests that the colorant moiety of BMAC is eliminated from the copolymer on account of the alkali treatment. On the other hand, any light beam having any wavelength was transmitted through the filtrate of the HBZ-PHM copolymer after the alkali treatment, and the colorant component was not liberated or released from the copolymer even in the case of the condition of pH of not less than 12 brought about by the alkali treatment. That is, it has been confirmed that the HBZ-PHM copolymer is stable against the pH change as compared with the BMAC copolymer, and the HBZ-PHM copolymer is scarcely affected by the pH change.

INDUSTRIAL APPLICABILITY

According to the present invention, the polymerizable UV-absorbing colorant monomer, which is stable even under alkaline conditions, is provided. The colorant compound of the present invention has, in its molecule, the benzophenone skeleton which has the capability to absorb the ultraviolet light, the azobenzene skeleton which has the capability to absorb the light in the blue region, and the polymerizable group. Therefore, the colorant compound of the present invention can be copolymerized with other polymerizable monomer to obtain the polymer, and the polymer is useful as the material, for example, for the intraocular lens.

The invention claimed is:

1. A compound represented by the following general formula (1):

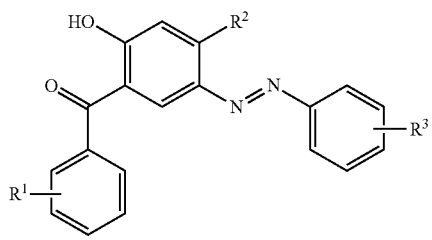

(1)

wherein $R^1$ is a hydrogen atom, a hydroxy group, a carboxy group, an alkyl group having 1 to 8 carbon atoms, an alkoxy group having 1 to 8 carbon atoms, a sulfonic acid group, or a benzyloxy group, $R^2$ is a hydrogen atom, a hydroxy group, or an alkoxy group having 1 to 4 carbon atoms, and $R^3$ is represented by the following formula (2):

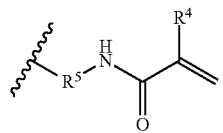

(2)

wherein $R^4$ is a hydrogen atom or a methyl group, and $R^5$ is an alkylene group having 1 to 4 carbon atoms which may have a substituent or substituents.

2. The compound according to claim 1, wherein $R^1$ is a hydrogen atom, a methyl group, or an ethyl group.

3. The compound according to claim 1, wherein $R^2$ is a hydrogen atom, a hydroxy group, a methoxy group, or an ethoxy group.

4. A polymer comprising the compound as defined in claim 1 and one species or two or more species of other polymerizable monomers which are copolymerized with each other.

5. An intraocular lens comprising the polymer as defined in claim 4 which is molded.

6. The compound of claim 1, wherein $R^5$ is ethylene which may have a substituent or substituents.

* * * * *